United States Patent
Buckland et al.

(10) Patent No.: US 8,529,062 B2
(45) Date of Patent: *Sep. 10, 2013

(54) SYSTEMS FOR EXTENDED DEPTH FREQUENCY DOMAIN OPTICAL COHERENCE TOMOGRAPHY (FDOCT) AND RELATED METHODS

(71) Applicant: Bioptigen, Inc., Durham, NC (US)

(72) Inventors: Eric L. Buckland, Hickory, NC (US); Bradley A. Bower, Hillsborough, NC (US)

(73) Assignee: Bioptigen, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/686,214

(22) Filed: Nov. 27, 2012

(65) Prior Publication Data

US 2013/0100406 A1  Apr. 25, 2013

Related U.S. Application Data

(63) Continuation of application No. 12/867,891, filed on Sep. 22, 2010, now Pat. No. 8,348,427.

(60) Provisional application No. 61/244,718, filed on Sep. 22, 2009, provisional application No. 61/254,465, filed on Oct. 23, 2009.

(51) Int. Cl.
*A61B 3/14* (2006.01)
*A61B 3/00* (2006.01)
*G01B 11/02* (2006.01)

(52) U.S. Cl.
USPC ............................ 351/206; 351/246; 356/497

(58) Field of Classification Search
USPC .................................. 351/200–246
See application file for complete search history.

(56) References Cited

U.S. PATENT DOCUMENTS

| | | | |
|---|---|---|---|
| 4,834,474 A | 5/1989 | George et al. | |
| 5,220,450 A | 6/1993 | Iizuka | |
| 7,019,838 B2 | 3/2006 | Izatt et al. | |
| 7,224,867 B2 | 5/2007 | Mossberg | |
| 7,336,366 B2 | 2/2008 | Choma et al. | |
| 7,400,410 B2 | 7/2008 | Baker et al. | |
| 7,519,248 B2 | 4/2009 | Iazikov et al. | |
| 7,602,500 B2 | 10/2009 | Izatt et al. | |

(Continued)

FOREIGN PATENT DOCUMENTS

| | | |
|---|---|---|
| EP | 1 870 029 A1 | 6/2006 |
| EP | 1 870 030 A1 | 6/2006 |
| EP | 1 870 028 A1 | 12/2007 |

OTHER PUBLICATIONS

Akcay et al. "Spectral shaping to improve the point spread function in optical coherence tomography", Oct. 15, 2003, vol. 28, No. 20, Optics Letters, pp. 1921-1923.

(Continued)

*Primary Examiner* — MoHammed Hasan
(74) *Attorney, Agent, or Firm* — Myers Bigel Sibley & Sajovec

(57) ABSTRACT

Systems for extended depth frequency domain optical coherence tomography are provided including a detection system configured to sample spectral elements at substantially equal frequency intervals, wherein a spectral width associated with the sampled spectral elements is not greater than one-half of the frequency interval. Related methods are also provided herein.

19 Claims, 28 Drawing Sheets

(56) References Cited

U.S. PATENT DOCUMENTS

| | | | |
|---|---|---|---|
| 7,719,692 B2 | 5/2010 | Izatt et al. | |
| 7,742,174 B2 | 6/2010 | Izatt et al. | |
| 7,744,221 B2 | 6/2010 | Wei et al. | 351/246 |
| 7,830,525 B2 | 11/2010 | Buckland et al. | 356/479 |
| 7,843,572 B2 | 11/2010 | Tearney et al. | |
| 8,033,665 B2 | 10/2011 | Ferguson et al. | 351/221 |
| 8,042,944 B2 | 10/2011 | De Vries et al. | 351/221 |
| 8,348,427 B2 * | 1/2013 | Buckland et al. | 351/206 |
| 2004/0066489 A1 | 4/2004 | Benedikt et al. | |
| 2004/0239943 A1 | 12/2004 | Izatt et al. | |
| 2007/0030483 A1 | 2/2007 | Everett et al. | |
| 2007/0053635 A1 | 3/2007 | Iazikov et al. | |
| 2007/0076217 A1 | 4/2007 | Baker et al. | |
| 2007/0291277 A1 | 12/2007 | Everett et al. | |
| 2008/0002183 A1 | 1/2008 | Yatagai et al. | |
| 2008/0106696 A1 | 5/2008 | Buckland et al. | |
| 2008/0170219 A1 | 7/2008 | Sarunic et al. | |
| 2008/0181477 A1 | 7/2008 | Izatt et al. | |
| 2010/0094576 A1 | 4/2010 | de Boer et al. | |

OTHER PUBLICATIONS

Bajraszewski et al. Improved spectral optical coherence tomography using optical frequency comb,Mar. 17, 2008, vol. 16, No. 6, Optics Express, pp. 4163-4176.

Balmer et al. "Diagnosis and current management of retinoblastoma," *Oncogene* 25, 5341-5349 (2006), Mar. 2008.

Brancato et al. "Optical coherence tomography (OCT) in retinal angiomatous proliferation (RAP)," *European Journal of Ophthalmology*, vol. 12, No. 6, 2002, pp. 467-472, Sep. 2003.

Broaddus et al. "Incidence of retinoblastoma in the USA: 1975-2004," *British Journal of Ophthalmology* 2009; 93, pp. 21-23, Sep. 2003.

Choma at al. "Sensitivity advantage of swept source and Fourier domain optical coherence tomography", Sep. 8, 2003, vol. 11, No. 18, Optics Express, pp. 2183-2189.

Congdon et al. "Causes and prevalence of visual impairment among adults in the United States," Arch. Ophthalmol., Vo. 122, Apr. 2004, pp. 477-485.

de Boer et al. "Improved signal-to-noise ratio in spectral-domain compared with time-domain optical coherence tomography," Nov. 1, 2003, vol. 28, No. 21, Optics Letters, pp. 2067-2069.

Glasier et al. "High Resolution Ultrasound with Doppler: a diagnostic adjunct in orbital and ocular lesions in children", *Pediatric Radiology* 22, 174-178 (1992), Nov. 2003.

Goes, "Visual Results Following Implantation of a Refractive Multifocal IOL in One Eye and a Diffractive Multifocal IOL in the Contralateral Eye," *Journal of Refractive Surgery*, vol. 24 Mar. 2008, pp. 300-305.

Grulkowski et al. "Anterior segment imaging with Spectral OCT system using a high-speed CMOS camera", Mar. 16, 2009, vol. 17, No. 6 Optics Express, pp. 4842-4858.

Hee et al. "Optical Coherence Tomography of the Human Retina," *Arch. Ophthalmol.*, vol. 113, Mar. 2005, pp. 325-332.

Hu at al. "Fourier domain optical coherence tomography with a linear-in-wavenumber spectrometer", Dec. 15, 2007, vol. 32, No. 24, Optics Letters, pp. 3525-3527.

Huang et al. "Optical Coherence Tomography.," Science, vol. 264, Nov. 22, 1991, pp. 1178-1181.

International Preliminary Report on Patentability corresponding to International Applicaton No. PCT/JP2005/004800; Date of Issuance of this report: Feb. 13, 2007.

International Search Report and Written Opinion of the International Searching Authority corresponding to International Application No. PCT/US2010/049793; Date of Mailing: Apr. 8, 2011; 15 pages.

Invitation to Pay Additional Fees for International Application No. PCT/US2010/049793; Date of Mailing: Feb. 2, 2011; 7 pages.

Izatt et al. "High-speed In Vivo retinal imaging with optical coherence tomography," *Investigative Ophthalmology & Visual Science*, Mar. 15, 1994, vol. 35, No. 4, p. 1729.

Izatt et al. "In Vivo Imaging of the Human Retina With Optical Coherence Tomography," *Investigative Ophthalmology & Visual Science* vol. 34, p. 761 (1993), Mar. 1994.

Izatt et al. "Optical coherence microscopy in scattering media", Optics Letters, vol. 19, No. 8, Apr. 15, 1994, pp. 590-592.

Izatt et al. "Quantitative assessment of cataract development with optical coherence domain reflectometry and optical coherence tomography," *Investigative Ophthalmology & Visual Science* vol. 33, p. 1300 (1992).

Izatt et al. "Theory of Optical Coherence Tomography," in *Optical Coherence Tomography: Technology and Applications*, Springer, (Eds.)W. Drexler, and J. G. Fujimoto, 2008, ISBN 978-3-540-77549-2, pp. 47-72, Jun. 2012.

Izatt et al. "Micrometer-Scale Resolution Imaging of the Anterior Eye In Vivo With Optical Coherence Tomography," Arch Ophthalmol, vol. 112, Dec. 1994, pp. 1584-1589.

Leitgeb et al. "Performance of fourier domain vs. time domain optical coherence tomography", Apr. 21, 2003, vol. 11, No. 8, Optics Express, pp. 889-894.

Leitgeb et al. "Phase-shifting algorithm to achieve high-speed long-depth-range probing by frequency-domain optical coherence tomography", Nov. 15, 2003, vol. 28, No. 22, Optics Letters, pp. 2201-2203.

Mafee et al. "Retinoblastoma and Simulating Lesions: Role of CT and MR Imaging", Imaging in Ophthalmology, Part II; *Radiologic Clinics of North America*, vol. 25, No. 4, Jul. 1987, pp. 667-682.

Monteiro et al. "Optical coherence tomography analysis of axonal loss in band atrophy of the optic nerve," *British Journal of Ophthalmology* 2004; 88: 896-899.

Peyster et al. "Intraocular Tumors: Evaluation with MR Imaging[1]", *Radiology*, Sep. 1988; 168: 773-779.

Puliafito et al. "Imaging of Macular Diseases with Optical Coherence Tomography," *Ophthalmology*, vol. 102, No. 2, Feb. 1995, pp. 217-229.

Quigley et al. "The number of people with glaucoma worldwide in 2010 and 2020," *British Journal of Ophthalmology* 2006 90: 262-267.

Rein et al. "The Economic Burden of Major Adult Visual Disorders in the United States," *Arch. of Ophthalmol.*, vol. 124, Dec. 2006, pp. 1754-1760.

Takada, "High-Resolution OFDR with Incorporated Fiber-Optic Frequency Encoder", IEEE Photonics Technology Letters, vol. 4, No. 9, Sep. 1992, pp. 1069-1072.

Tao et al. "High-speed complex conjugate resolved retinal spectral domain optical coherence tomography using sinusoidal phase modulation," Optics Letters, vol. 32, No. 20, Oct. 15, 2007, pp. 2918-2920.

Traub, "Constant-dispersion grism spectrometer for channeled spectra," *Journal of the Optical Society of America* A 7, pp. 1779-1791, Sep. 1990, vol. 7, No. 9, Woodbury, NY, US.

Tripathi et al. "Spectral shaping for non-Gaussian source spectra in optical coherence tomography", Optics Letters, vol. 27, No. 6, Mar. 15, 2002, pp. 406-408.

Werner et al. "Phakic Posterior Chamber Intraocular Lenses," International Ophthalmology Clinics 41, pp. 153-174 (2001), Feb. 2005.

Wollstein et al. "Ultrahigh-Resolution Optical Coherence Tomography in Glaucoma," *Ophthalmology* vol. 112, No. 2, Feb. 2005; pp. 229-237.

Wollstein et al. "Comparison of Three Optical Coherence Tomography Scanning Areas for Detection of Glaucomatous Damage," American Journal of Ophthalmology, vol. 139, No. 1; Jan. 2005; pp. 39-43.

Yun et al. "High-speed spectral-domain optical coherence tomography at 1.3 μm wavelength," *Opt Express*. Dec. 29, 2003; 11 (26): 3598-3604.

Baikoff, Phakic anterior chamber Intraocular lenses, International Ophthalmology Clinics, 31(1), p. 75-86 (1991), Aug. 1996.

Hee et al., "Optical Coherence Tomography of Age-related Macular Degeneration and Choroidal Neovascularization", *Ophthalmology*, vol. 103, No. 8, Aug. 1996; pp. 1260-1270.

International Search Report and Written Opinion of the International Searching Authority corresponding to International Application No. PCT/US2010/053702, Date of Mailing: Mar. 10, 2011; 16 pages.

Invitation to Pay Additional Fees corresponding to International Application No. PCT/US2010/053702; Date of Mailing: Dec. 22, 2010; 7 pages.

Werner et al. "Phakic anterior chamber intraocular lenses," International Ophthalmology Clinics 41, 133-152 (2001), Dec. 2010.

Notification Concerning Transmittal of International Preliminary Report on Patentability, PCT/US2010/049793, Apr. 5, 2012.

Notification Concerning Transmittal of International Preliminary Report on Patentability, PCT/US2010/053702, May 3, 2012.

Bajraszewski T. et al., "Improved spectral optical coherence tomography using optical frequency comb", *Optics Express*, Mar. 17, 2008, vol. 16, No. 6, 4163-4176.

Grulkowski I. et al., "Anterior segment imaging with Spectral OCT system using a high-speed CMOS camera", *Optics Express*, Mar. 16, 2009, vol. 17, No. 6, 4842-4858.

* cited by examiner

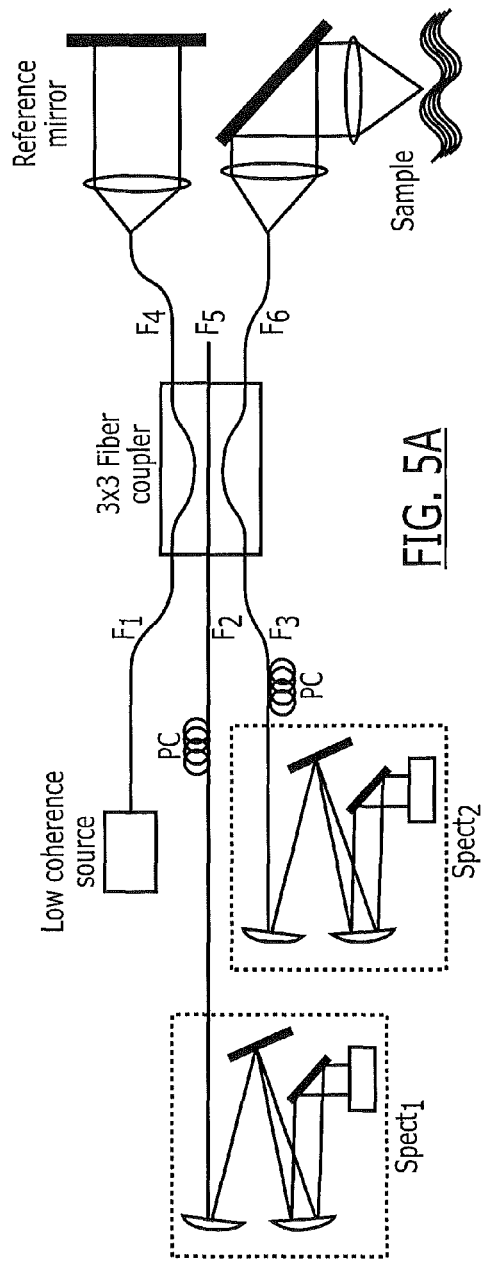
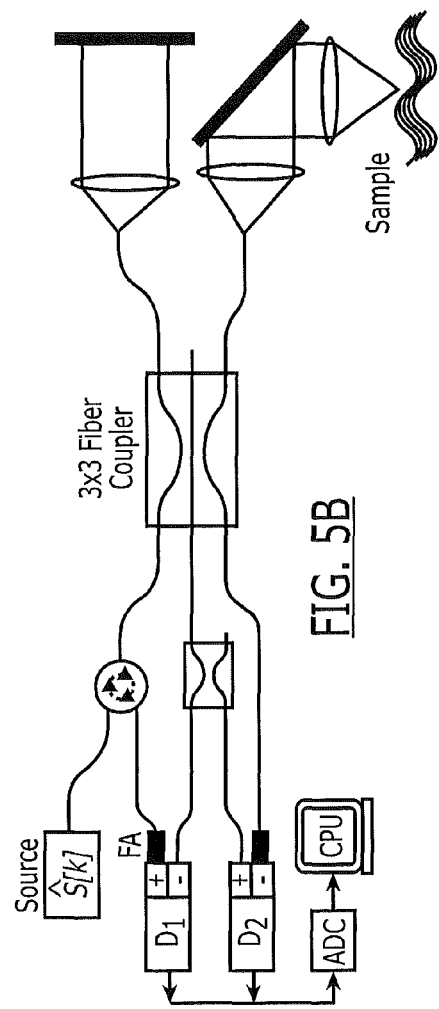
FIG. 5A
FIG. 5B

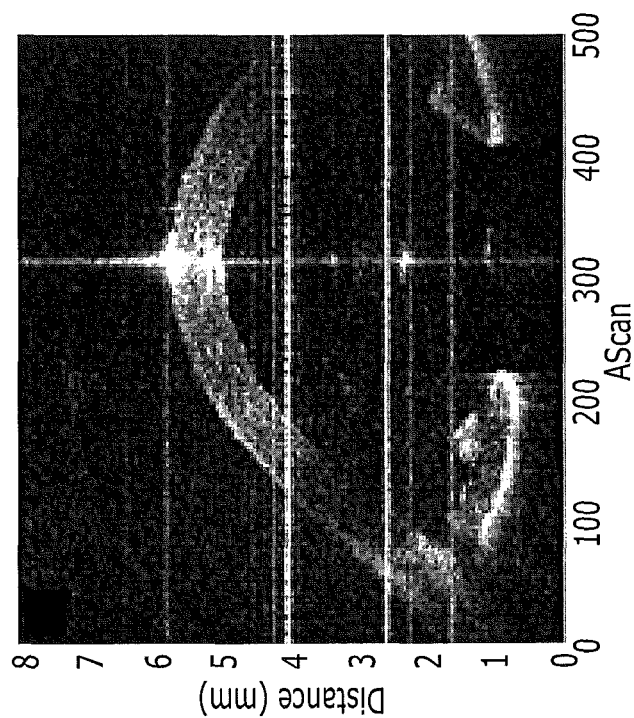
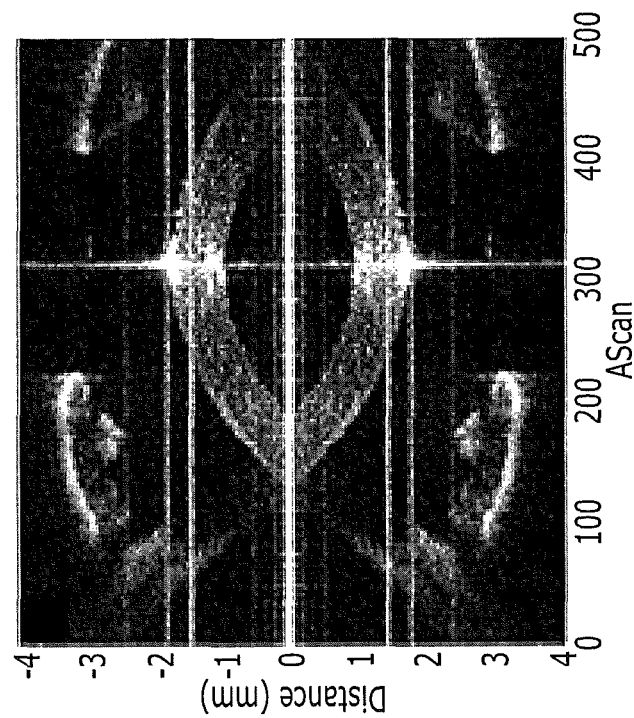
FIG. 5D
FIG. 5C

| | | 3.5 | 7 | 8 | 9 | 10 |
|---|---|---|---|---|---|---|
| | Single-sided depth (air, mm) | 3.5 | 7 | 8 | 9 | 10 |
| | Double Sided Depth (air, mm) | 7 | 14 | 16 | 18 | 20 |
| | d_v (GHz) | 21.43 | 10.71 | 9.38 | 8.33 | 7.50 |
| 4096 | spectrometer bandwidth (nm) | 206.44 | 103.22 | 90.32 | 80.28 | 72.25 |
| 3 dB | usable source be (nm) | 128.40 | 64.20 | 56.17 | 49.93 | 44.94 |
| um | resolution (um) | 2.42 | 4.85 | 5.54 | 6.24 | 6.93 |
| 840 | central wavelength (nm) | | | 840 | | |
| GRISM | prism material | | | Schott P-SF68 | | |
| | prism index | | | 2.0052 | | |
| | prism AOI (radians) | pi/8 | pi/8 | pi/8 | pi/8 | pi/8 |
| | prism vertex angle (radians) | 0.36 | 0.66 | 0.65 | 0.65 | 0.65 |
| | grating material | | | Schott B-270 | | |
| | grating index | | | 1.523 | | |
| | grating pitch (1/mm) | 450 | 400 | 340 | 300 | 270 |
| | prism spot (mm) | 25 | 25 | 25 | 25 | 25 |
| | focal length (mm) | 100 | 220 | 330 | 445 | 575 |
| | k pixel.shift max (pix) | 0.42 | 0.49 | 0.39 | 0.33 | 0.37 |

FIG. 17

SYSTEMS FOR EXTENDED DEPTH FREQUENCY DOMAIN OPTICAL COHERENCE TOMOGRAPHY (FDOCT) AND RELATED METHODS

CLAIM OF PRIORITY

The present application is a continuation of U.S. patent application Ser. No. 12/887,891, filed Sep. 22, 2010, now U.S. Pat. No. 8,348,427 B2 which claims priority to U.S. Provisional Application No. 61/244,718, filed Sep. 22, 2009 and U.S. Provisional Application No. 61/254,465, filed Oct. 23, 2009, the disclosures of which are hereby incorporated herein by reference as if set forth in their entirety.

FIELD

The present inventive concept generally relates to imaging and, more particularly, to frequency domain optical coherence tomography (FDOCT) and related systems and methods.

BACKGROUND

Optical coherence tomography (OCT) is a noninvasive imaging technique that provides microscopic tomographic sectioning of biological samples. By measuring singly backscattered light as a function of depth, OCT fills a valuable niche in imaging of tissue ultrastructure, providing subsurface imaging with high spatial resolution (−2.0-10.0 µm) in three dimensions and high sensitivity (>110 dB) in vivo with no contact needed between the probe and the tissue.

In biological and biomedical imaging applications, OCT allows for micrometer-scale imaging non-invasively in transparent, translucent, and/or highly-scattering biological tissues. The longitudinal ranging capability of OCT is generally based on low-coherence interferometry, in which light from a broadband source is split between illuminating the sample of interest and a reference path. The interference pattern of light reflected or backscattered from the sample and light from the reference delay contains information about the location and scattering amplitude of the scatterers in the sample. In time-domain OCT (TDOCT), this information is typically extracted by scanning the reference path delay and detecting the resulting interferogram pattern as a function of that delay. The envelope of the interferogram pattern thus detected represents a map of the reflectivity of the sample versus depth, generally called an A-scan, with depth resolution given by the coherence length of the source. In OCT systems, multiple A-scans are typically acquired while the sample beam is scanned laterally across the tissue surface, building up a two-dimensional map of reflectivity versus depth and lateral extent typically called a B-scan. The lateral resolution of the B-scan is approximated by the confocal resolving power of the sample arm optical system, which is usually given by the size of the focused optical spot in the tissue.

The time-domain approach used in conventional OCT, including commercial instruments, such as Carl Zeiss Meditec's Stratus® and Visante® products, has been successful in supporting biological and medical applications, and numerous in vivo human clinical trials of OCT reported to date have utilized this approach.

An alternate approach to data collection in OCT has been shown to have significant advantages in increased signal-to-noise ratio (SNR). This approach involves acquiring the interferometric signal generated by mixing sample light with reference light at a fixed group delay as a function of optical wavenumber. Two distinct methods have been developed which use this Fourier domain OCT (FD-OCT) approach. The first, generally termed Spectral-domain or spectrometer-based OCT (SDOCT), uses a broadband light source and achieves spectral discrimination with a dispersive spectrometer in the detector arm. The second, generally termed swept-source OCT (SSOCT) or optical frequency-domain imaging (OFDI), time-encodes wavenumber by rapidly tuning a narrowband source through a broad optical bandwidth. Both of these techniques may allow for a dramatic improvement in SNR of up to 15.0-20.0 dB over time-domain OCT, because they typically capture the A-scan data in parallel. This is in contrast to previous-generation time-domain OCT, where destructive interference is typically used to isolate the interferometric signal from only one depth at a time as the reference delay is scanned.

FDOCT systems are discussed below with respect to FIGS. 1 through 3. Referring first to FIG. 1, a block diagram illustrating a Fourier domain OCT system in accordance with some embodiments of the present invention will be discussed. As illustrated in FIG. 1, the system includes a broadband source 100, a reference arm 110 and a sample arm 140 coupled to each other by a beamsplitter 120. The beamsplitter 120 may be, for example, a fiber optic coupler or a bulk or micro-optic coupler without departing from the scope of the present invention. The beamsplitter 120 may provide from about a 50/50 to about a 90/10 split ratio. As further illustrated in FIG. 1, the beamsplitter 120 is also coupled to a wavelength or frequency sampled detection module 130 over a detection path 106 that may be provided by an optical fiber.

As further illustrated in FIG. 1, the source 100 is coupled to the beamsplitter 120 by a source path 105. The source 100 may be, for example, a SLED or tunable source. The reference arm 110 is coupled to the beamsplitter over a reference arm path 107. Similarly, the sample arm 140 is coupled to the beamsplitter 120 over the sample arm path 108. The source path 105, the reference arm path 107 and the sample arm path 108 may all be provided by optical fiber.

As further illustrated in FIG. 1, the sample arm 140 may include scanning delivery optics and focal optics 160. Also illustrated in FIG. 1 is the reference plane 150 and a representation of an OCT imaging window 700.

Referring now to FIG. 2, a block diagram of an FDOCT retinal imaging system will be discussed. As illustrated in FIG. 2, in an FDOCT retinal imaging system, the reference arm 110 may further include a collimator assembly 280, a variable attenuator 281 that can be neutral density or variable aperture, a mirror assembly 282, a reference arm variable path length adjustment 283 and a path length matching position 250, i.e. optical path length reference to sample. As further illustrated, the sample arm 240 may include a dual-axis scanner assembly 290 and a variable focus objective lens 291.

The sample in FIG. 2 is an eye including a cornea 295, iris/pupil 294, ocular lens 293 and retina 296. A representation of an OCT imaging window 270 is illustrated near the retina 296. The retinal imaging system relies in the optics of the subject eye, notably cornea 295 and ocular lens 293, to image the posterior structures of the eye.

Referring now to FIG. 3, a block diagram illustrating a FDOCT cornea imaging system will be discussed. As illustrated therein, the system of FIG. 3 is very similar to the system of FIG. 2. However, the objective lens variable focus need not be included, and is not included in FIG. 3. The anterior imaging system of FIG. 3 images the anterior structures directly, without reliance on the optics of the subject to focus on the anterior structures.

In both spectrometer-based and swept-source implementations of FDOCT, light returning from all depths is generally collected simultaneously, and is manifested as modulations in the detected spectrum. Transformation of the detected spectrum from wavelength to wavenumber (or frequency), correction for dispersion mismatches between the sample and reference arms, and Fast Fourier transformation typically provides the spatial domain signal or "A-scan" representing depth-resolved reflectivity of the sample. The uncorrected A-scan may also include a strong DC component at zero pathlength offset, so-called "autocorrelation" artifacts resulting from mutual interference between internal sample reflections, as well as both positive and negative frequency components of the depth-dependent cosine frequency interference terms. Because of this, FDOCT systems typically exhibit a "complex conjugate artifact" due to the fact that the Fourier transform of a real signal, the detected spectral interferogram, is typically Hermitian symmetric, i.e., positive and negative spatial frequencies are not independent. As a consequence, sample reflections at a positive displacement, relative to the reference delay, typically cannot be distinguished from reflections at the same negative displacement, and appear as upside-down, overlapping images on top of genuine sample structure, which generally cannot be removed by image processing.

The maximum single-sided imaging depth available in SDOCT is governed by the spectral sampling interval. The maximum single-sided imaging depth is inversely proportional to the spectral sampling interval. With a fixed number of sampled spectral elements, there is an inverse relationship between the maximum imaging depth and the minimum axial resolution of the imaging system. In commercial FDOCT systems at 830 nm and 1300 nm reported to date, the single-sided imaging depth has been limited to approximately 4 mm. Time domain imaging has been used for greater imaging depths.

The finite spectral resolution of any real FDOCT system, whether governed by the linewidth of a swept laser source in SSOCT, or the geometric optical performance of the spectrometer convolved with the finite pixel size of the detector array in SDOCT, gives rise to a sensitivity "falloff" with imaging depth into the sample. It is common to have greater than 6 dB degradation in signal-to-noise from the position of zero reference delay to the position of maximum single-sided depth. This sensitivity "falloff" limits the portion of the single-sided depth useful for imaging.

To reduce the impact of these limitations in FDOCT imaging, imaging is commonly performed with the entire sample either above or below the reference position, limiting the available imaging depth to between 2 mm and 4 mm, and placing the sample region of interest close to the zero reference delay position.

Each of these constraints poses limitations on the application of FDOCT to clinical ophthalmology. Imaging systems have generally been dedicated to imaging of specific anatomy, such as retina or cornea, where the mirror image artifacts do not fold over onto images of the region of interest. Utility to image deeper anatomic structures, such as the choroid, has been limited by sensitivity "falloff".

Addressing these limitations opens significant new application areas for FDOCT, particularly in ophthalmology. Full range volumetric anterior segment imaging (cornea to lens) for improved diagnosis of narrow angle glaucoma is enabled at speeds 20 times greater and resolutions four times finer than time domain implementations. Real-time image guided surgery, for anterior chamber, cataract, or retina, is enabled by allowing placement of a deep imaging window at any position within the sample, without concern for confounding mirror image artifacts or signal "falloff." Images of the entire eye may be acquired, enabling for the first time modeling in three dimensions the entire optical structure of the eye and enabling whole-eye biometry.

SUMMARY

Some embodiments discussed herein provide extended depth Fourier domain optical coherence tomography imaging systems including a detection system configured to sample spectral elements at substantially equal frequency intervals, wherein a spectral width associated with the sampled spectral elements is not greater than one-half of the frequency interval.

In further embodiments, the spectral width associated with the sampled spectral elements may be approximately equal to one-half of the frequency interval.

In still further embodiments, the extended depth Fourier domain optical coherence tomography imaging system may be an ophthalmic imaging system configured to image a region of a sample with optimized depth field of view and image resolution. In certain embodiments, the sample is an eye. Some embodiments include at least one adjustable imaging window that defines an area of the eye to be imaged. The system may be configured to image structures of the eye in a wavelength range of from about 800 nm to about 1200 nm.

In some embodiments, the system may be configured to have a single-sided imaging depth of about 7.0 mm and a complex conjugate resolved image depth of about 14 mm.

In further embodiments, the system may include a combiner configured to connect elements of the system; and a broadband optical source coupled to the detection system through the combiner. The combiner may be a fiber optic coupler and the broadband optical source may include a superluminescent diode. The splitting ratio of the combiner may be selected to optimize power to a sample and signal to noise ratio of the detection system. The splitting ratio of the combiner may be a ratio of 80/20, wherein 20 percent of source light is directed to the sample and 80 percent of the source light is directed to a reference arm.

In still further embodiments, the system may include an optical reflector coupled to the detection system and the broadband optical source through the combiner by a reference arm. The reference arm may be adjustable and the optical reflector may be a phase modulated optical reflector.

In some embodiments, the detection system may be a k-linear spectrometer. In certain embodiments, the k-linear spectrometer may be a chirped grating or a GRISM.

In further embodiments, the system may include a periodic optical filter between the broadband optical source and the detection system. The optical filter may be a Fabry-Perot etalon.

In still further embodiments, the broadband optical source may include a swept comb source including a swept source laser and an optical filter. The optical filter may be a Fabry-Perot etalon. The swept comb source may include an optical output that is coupled to an acquisition trigger circuitry.

In some embodiments, the system may include a circulator and the swept comb source may be coupled to the combiner through the circulator. The combiner may include a single mode coupler with a coupling ratio between 50:50 and 90:10.

In further embodiments, the detection system includes a triggered balanced heterodyne detection system.

Still further embodiments provide methods for imaging over an extended depth using the extended depth fourier domain optical coherence tomography imaging system. In certain embodiments, the methods are for imaging an eye over an extended depth.

Some embodiments provide extended depth Fourier domain optical coherence tomography imaging systems including an adjustable detection system configured to sample spectral elements at substantially equal frequency intervals, wherein the frequency interval is adjustable.

Further embodiments provide extended depth Fourier domain optical coherence tomography imaging systems including a detection system configured to sample spectral elements at substantially equal frequency intervals, wherein a spectral width of the sampled spectral element is not greater than one-half of the frequency intervals and wherein a mirror image artifact is substantially removed.

In still further embodiments, the Fourier domain optical coherence tomography system may be a Spectral-domain optical coherence tomography system and the mirror image artifact may be substantially removed using continuous phase modulation of the reference arm.

In some embodiments, the Fourier domain optical coherence tomography system may be a swept source optical coherence tomography system and the mirror image artifact may be substantially removed using a differential frequency shift between the reference arm and the sample arm. The swept source optical coherence tomography system may include an acousto-optic modulator in the reference arm an no acousto-optic modulator in the sample arm

BRIEF DESCRIPTION OF THE FIGURES

FIGS. 5A through 5E OCT systems and images acquired using these OCT ophthalmic imaging systems in accordance with some embodiments.

FIG. 17 is a table including various details with respect to SDOCT systems in accordance with various embodiments of the present inventive concept.

DETAILED DESCRIPTION OF EMBODIMENTS

Figure 1:
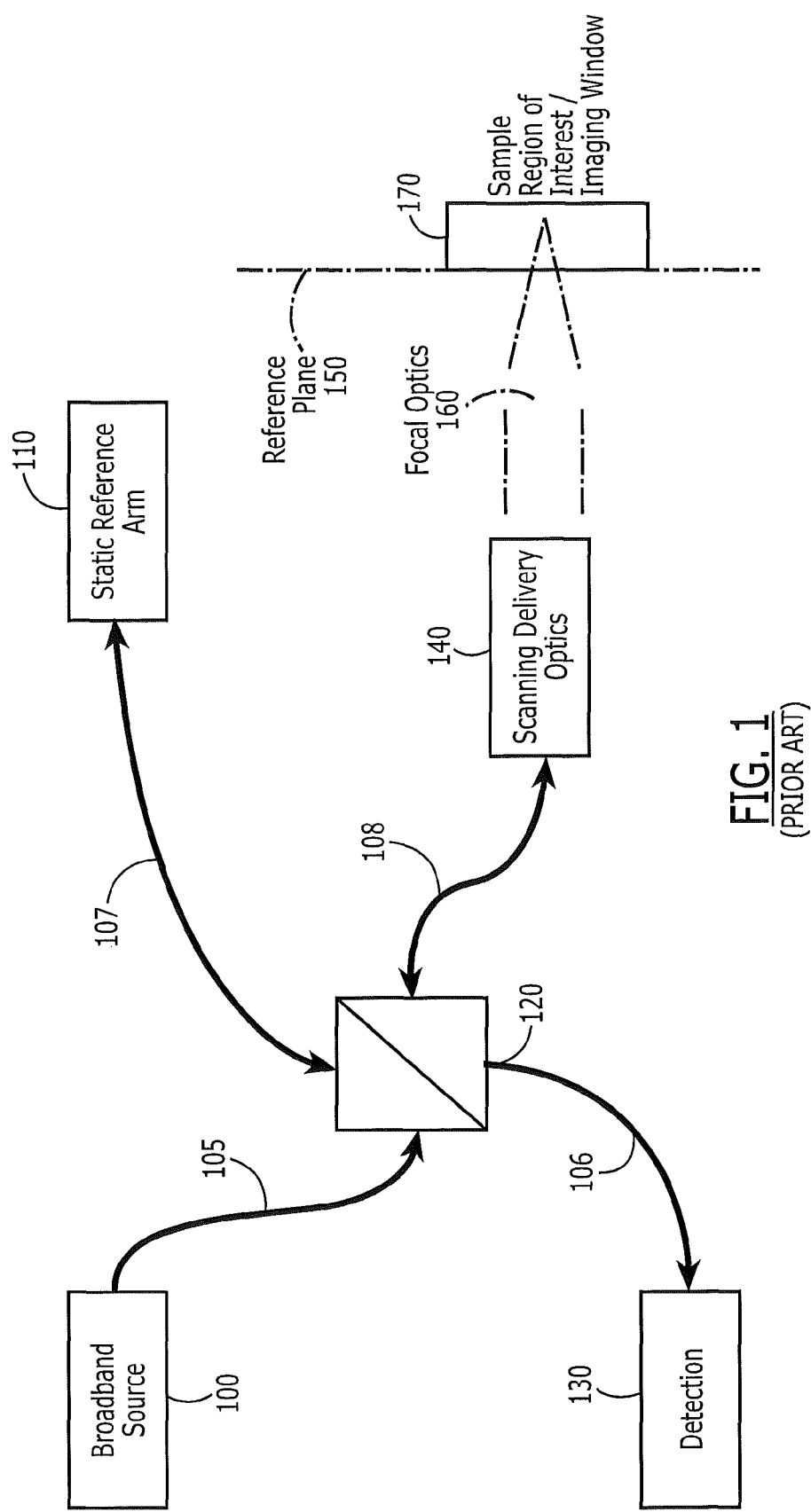
FIG. 1 is a block diagram illustrating a Fourier domain optical coherence tomography (OCT) imaging system.

Specific exemplary embodiments of the invention now will be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the particular exemplary embodiments illustrated in the accompanying drawings is not intended to be limiting of the invention. In the drawings, like numbers refer to like elements.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Embodiments discussed herein with respect to FIGS. 1 through 26 may be used in combination with many imaging systems for many applications and is not limited to the specific systems or applications discussed herein. For example, imaging systems discussed in commonly assigned U.S. Pat. Nos. 7,602,500; 7,742,174; and 7,719,692 and U.S. Patent Application Publications Nos. 2008/01606696 and 2008/0181477 may be used in combination with embodiments discussed herein. The disclosures of these patents and publications are hereby incorporated herein by reference as if set forth in its entirety.

As used herein, the term "spectral element" refers to the individually resolved samples of the interferometric spectrum as they are detected in an FDOCT system, the detected set of which forms the input to the Fourier transform operation; a spectral element is characterized by a finite wavelength range that is generally a continuous small fraction of the total bandwidth, an optical power, and a power spectral density (lineshape).

The first successful clinical application of OCT was for high-resolution imaging of ocular structure. OCT is well suited to ophthalmology because it is non-contact, easily adaptable to existing ophthalmic instrumentation, and most importantly, the axial imaging resolution is independent of the working distance. In the anterior eye, the micron-scale resolution of OCT imaging permits accurate biometry of large scale ocular structures and the evaluation of morphological changes associated with pathologies of the cornea, iris, and lens. In the retina, OCT is the only technique capable of resolving retinal substructure in cross section in the living eye. Imaging of retinal substructure is clinically relevant to the diagnosis and management of many ocular diseases. In many clinical trials of OCT, striking images have been obtained of a variety of retinal abnormalities, including macular defects and retinal nerve fiber atrophy. Retinal OCT has become well accepted as a clinical adjunct to conventional macular photography, as well as a very popular research tool.

As is well known in the art, Fourier domain optical coherence tomography (FDOCT) has become the standard of care in clinical ophthalmology for imaging of the retina. The theory and practice of FDOCT is well known and documented.

Several academic research groups have published detailed treatments of the dramatic 20-30 dB signal-to-noise predicted and actual performance improvement in FDOCT as compared to its time-domain counterparts. Despite this tremendous improvement, there are performance limitations in FDOCT which do not have analogs in previous time-domain systems. In both spectrometer-based (SDOCT) and swept-source (SSOCT) implementations of FDOCT, the wavenumber (k) resolved receiver current can be represented by equation (1) set out below:

$$i(k)=\tfrac{1}{2}\rho S(k)[R_R+R_S+2\sqrt{R_R R_S}\cos(2kz_0+\phi)] \quad (1)$$

where $\rho$ is the receiver element responsivity, $S(k)$ is the light source spectrum, $R_R$ and $R_S$ are the received power from the reference and sample arms, respectively, $z_0$ is the pathlength difference between the reference delay and a target reflection in the sample ($2z_o$ is the round-trip pathlength difference), and $\phi$ is the phase offset of the interferometer at zero pathlength optical delay. As in time domain OCT, the axial imaging resolution $\Delta z$ is defined by the source center wavelength $\lambda_0$ and FWHM bandwidth $\Delta\lambda$ as shown in equation (2) set out below:

$$\Delta z = \frac{2\ln(2)}{\pi}\frac{\lambda_0^2}{\Delta\lambda} \quad (2)$$

In FDOCT, light returning from all depths is collected simultaneously, and is manifested as modulations in the detected spectrum. Transformation of the detected spectrum from wavelength to wavenumber, correction for dispersion mismatches between the sample and reference arms, and Fast Fourier transformation provides the spatial domain signal or "A-scan" representing depth-resolved reflectivity of the sample.

Figures 4A, 4B:
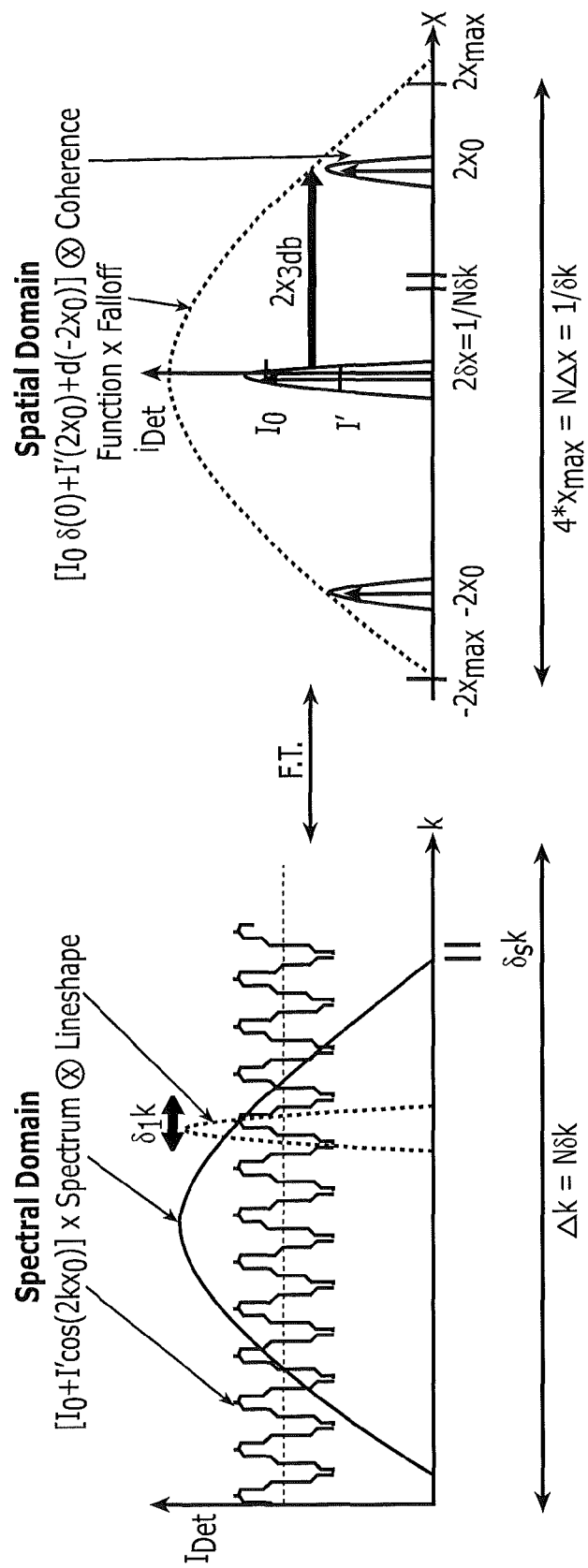
FIGS. 4A and 4B are graphs illustrating the spatial and spectral domain, respectively, that illustrate conceptually the effects that various parameters of the light source and spectral detection system in accordance with some embodiments.

FIGS. 4A and 4B illustrate conceptually the effects that various parameters of the light source and spectral detection system have on the transformed OCT signal. In both SDOCT and SSOCT systems, the detected spectral signal is composed of a DC term and cosinusoidal terms with depth-dependent frequency. This signal is enveloped by the source spectrum and convolved with the spectral resolution ($\delta_r k$) of the FDOCT system. In SSOCT, the spectral resolution $\delta_r k$ is limited by the instantaneous lineshape of the swept laser source, while in SDOCT, $\delta_r k$ is the spectral resolution of the spectrometer (which in turn may be described as a convolution of the geometric optic spectrometer resolution with the detector array pixel dimensions). The detected spectrum is sampled with spectral sampling interval $\delta_s k$ into N spectral channels, each of these channels comprising a unique spectral element. The Fourier transform of the detected spectral signal, i.e. the set of spectral elements, includes a strong DC component at zero pathlength offset, as well as both positive and negative frequency components of the depth-dependent cosine frequency terms located at positions $\pm 2x_0$. The shape of each peak is defined by the coherence function of the source, given by the inverse Fourier transform of its total detected power spectral density; as in time-domain OCT, the axial imaging resolution is inversely proportional to the total detected spectral bandwidth of the light source.

Figure 5E:
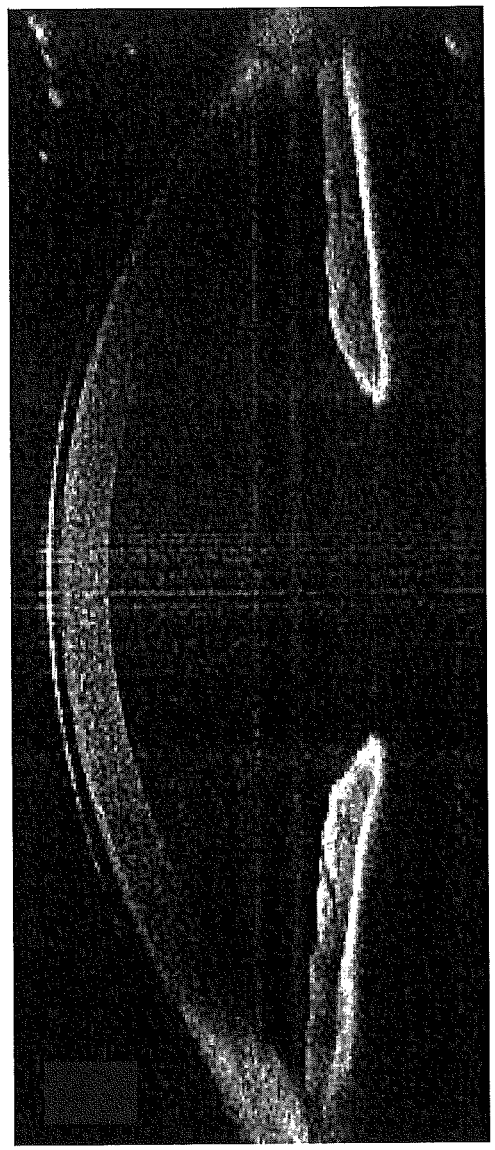

There are at least three important limitations which are novel in FDOCT: complex conjugate artifact, maximum imaging depth, and sensitivity falloff. The presence in the spatial-domain A-scan data of both positive and negative frequency components of the spectral interferometric signal gives rise to the so-called "complex conjugate artifact" which typically requires careful sample positioning to assure that overlapping negative frequency components do not interfere with the principal positive-frequency image as illustrated in FIG. 5C. Methods to reduce this "complex conjugate artifact" are now known in the art. In particular, FIG. 5A illustrates a 3×3 SDOCT system utilizing two spectrometers; FIG. 5B illustrates a 3×3 SSOCT system implementing DC signal subtraction with balanced photodiode detectors D1 and D2; FIGS. 5C and 5D illustrate unprocessed and complex conjugate resolved images of human anterior segment acquired in vivo with 3×3 SSOCT, using a first image processing method; and FIG. 5E illustrates improved complex conjugate artifact removal (better than 30 dB) obtained using a quadrature projection algorithm.

Figure 6:
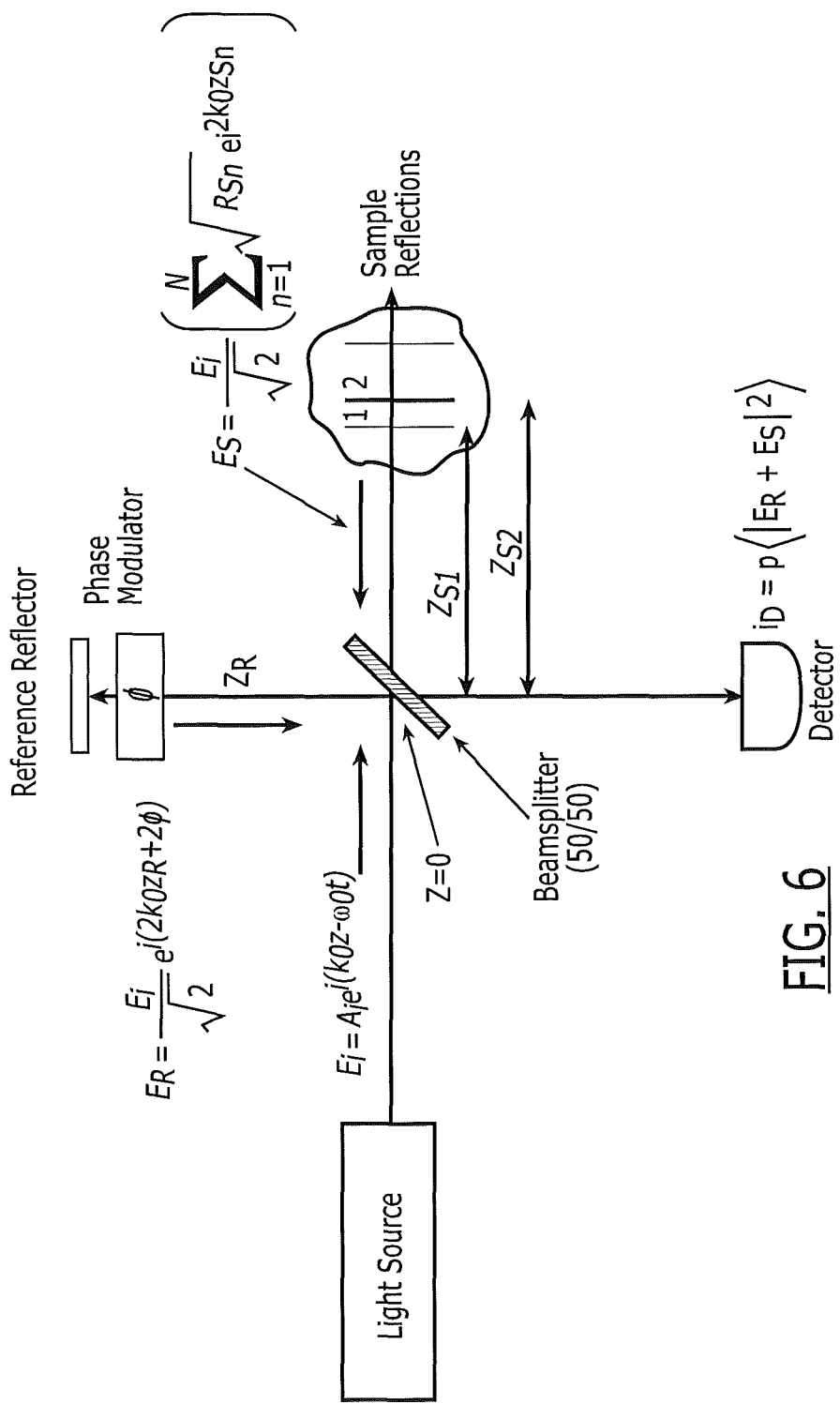
FIG. 6 is a block diagram illustrating an FDOCT interferometer having a variable round trip phase delay in the reference arm in accordance with some embodiments.

The complex conjugate artifact in FDOCT may also be removed by utilizing principles and techniques related to phase-shift interferometry. If the interferometer is modified to provide for the introduction of a variable single-pass phase delay φ (round-trip phase delay 2φ) between the reference and sample arms, then a set of spectral interferograms may be acquired with different phase delays which can be combined in signal processing to eliminate the undesired artifacts. For example, FIG. 6 illustrates an FDOCT interferometer with a variable phase modulator placed in the reference arm, such that the reference field returning from the reference arm is modified.

Various technical solutions to this complex conjugate artifact problem have been proposed by several groups, however all of those proposed to date require rather complicated schemes for acquisition of multiple interferometric spectra, and none have yet proven satisfactory for high duty cycle imaging. For ophthalmic imaging, the complex conjugate artifact necessitates maintaining very careful positioning of the patient to avoid overlapping upside-down images (difficult in some patients), and it precludes imaging tissues any thicker than the single-sided imaging depth $z_{max}$ defined next.

Due to spectral sampling considerations, the maximum single-sided imaging depth $z_{max}$ available in FDOCT is governed by the spectral sampling interval $\delta_s k$ or $\delta_s \lambda$, according to equation (3) set out below:

$$z_{max} = \frac{\pi}{2 \cdot \delta_s k} = \frac{\lambda_0^2}{4 \cdot \delta_s \lambda} \quad (3)$$

These expressions are given in terms of both wavenumber k ($=2\pi/\lambda$) and wavelength λ (with center wavelength $\lambda_0$). In FDOCT systems at 830 nm and 1300 nm reported to date, $z_{max}$ has been limited to approximately 4.0 mm.

The finite spectral resolution of any real FDOCT system, whether governed by the linewidth of a swept laser source in SSOCT, or the geometric optical performance of the spectrometer convolved with the finite pixel size of the detector array in SDOCT, gives rise to a falloff in sensitivity with imaging depth that is independent of light attenuation within the sample. More generally for both SDOCT and SSOCT systems, if an "effective" detector sampling resolution $\delta_r k$ or $\delta_r \lambda$ is defined which accounts for all effects limiting the spectral resolution of the sampled elements, a simpler expression can be derived for the falloff to the 6 dB SNR point as illustrated by equation (4) set out below:

$$z_{6\,dB} = \frac{2\ln(2)}{\delta_r k} = \frac{2\ln(2)}{\pi} \frac{\lambda_0^2}{\delta_r \lambda} \quad (4)$$

In typical FDOCT systems, the falloff phenomenon exacerbates the already-limited imaging depth $z_{max}$. In SSOCT systems, the spectral linewidth is a function of laser dynamics and the detector sampling architecture. In SDOCT systems, the spectral sampling interval $\delta_s k$ and spectral linewidth $\delta_r k$ are generally a function of spectrometer design. In a well-designed spectrometer with Nyquist sampling of the optics-limited resolution, $\delta_r k \geq 2 \delta_s k$. For the case of $\delta_r k = 2 \delta_s k$, equations (3) and (4) can be combined to obtain the useful rule of thumb for SDOCT systems illustrated by equation (5) set out below:

$$\frac{z_{6\,dB}}{z_{max}} \approx 0.44 \quad (5)$$

Thus, in practical SDOCT systems, as in most commercial ophthalmic SDOCT systems, the useful portion of the depth imaging range, defined as the 6 dB falloff point, is limited to approximately half of the range given by the spectral sampling, i.e. approximately 2.0 mm instead of 4.0 mm. This may be sufficient for imaging the normal retina, however it may preclude imaging structures above and below normal retina, for example, vitreous features, choroid, and deeply cupped optic nerve heads. It may also be insufficient for imaging almost any anterior segment structures besides the cornea without incurring upside-down artifacts.

The complex conjugate artifacts and falloff of sensitivity with imaging depth are fundamentally new limitations in FDOCT, which have not yet been successfully addressed by technical innovation. These phenomena represent significant limitations to the applicability of FDOCT techniques for ophthalmic diagnostics which require imaging of structures deeper than about 2.0 mm.

Figure 15:
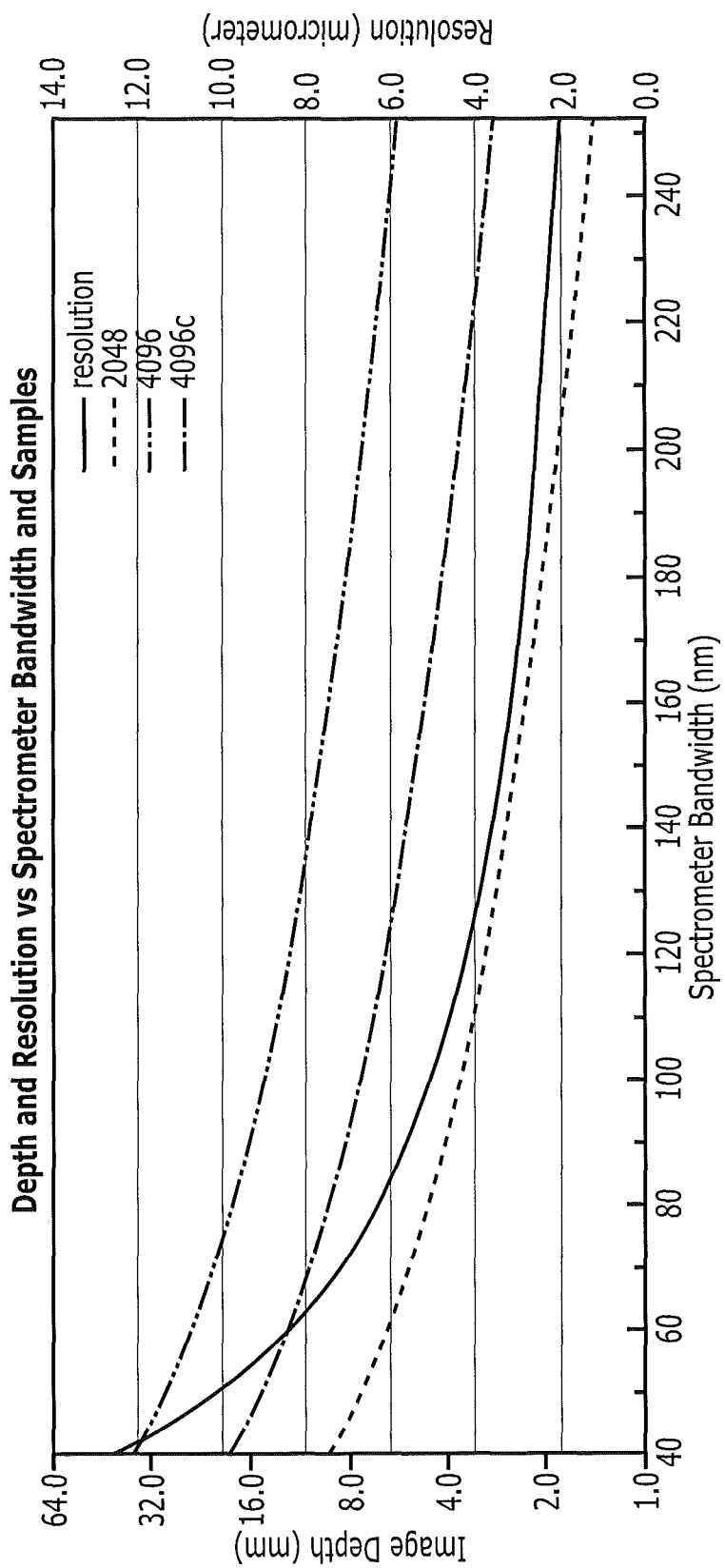
FIG. 15 is a graph illustrating depth and resolution vs. spectrometer bandwidth and samples for an extended depth FDOCT system in accordance with some embodiments discussed herein.

Three improvements may be combined for overcoming the limitations discussed above and enabling deep imaging FDOCT systems for new applications of FDOCT where increased depth and removal of mirror-image artifacts are desirable. Deep-imaging sampling architectures increase zmax. Modifying the sampled spectral bandwidth such that the bandwidth of the sampled element is less than the sampling interval reduces the deleterious effects of sensitivity falloff. Addition of phase information to the acquired spectrum provides information sufficient to remove complex conjugate artifacts. The combination of the latter two techniques enables system design to quadruple available imaging depth without impacting the axial resolution of the imaging system. Tailoring the sampling architecture to adjust the maximum imaging depth zmax requires a trade-off between axial resolution and maximum imaging depth, as shown in FIG. 15, as may be appropriate for the imaging of target structures. These techniques may be applied to either SDOCT or SSOCT implementations, and to implementations that combine elements of SDOCT and SSOCT. Further, in some cases these techniques may be applied dynamically, controlling $z_{max}$, complex-conjugate management, and falloff in situ to manage trade-offs in pixel resolution, region of subject focus, optical power on subject, and imaging speed as may be appropriate for specific objectives during the imaging process.

For a traditional volume phase holographic (VPH) grating based spectrometer design, the imaging depth, as measure in tissue of refractive index n, is related to the bandwidth and pixel count of the spectrometer as illustrated in equation (6) set out below:

$$z_{max} = \lambda_c^2 / 4n\lambda_s \quad (6)$$

Where
δ=spectrometer bandwidth (nm)
$\lambda_c$=source center wavelength (nm)
p=pixels (detector channels)
$\lambda_s$=spectrometer wavelength spacing=δ/p
n=index of refraction A key spectrometer design decision is to optimize for image resolution, by maximizing available bandwidth δ, or optimize for imaging depth, by minimize sampling interval $\lambda_s$.

With $\lambda_s = \delta/p$ equation (6) becomes:

$$Z = p\lambda_c^2/4n\delta \tag{7}$$

For fixed p, solving for δ in becomes:

$$\delta = p\lambda_c^2/4nZ \tag{8}$$

Alternatively, for fixed δ and solving for $\lambda_c$ in nanometers leads to:

$$\lambda_c = \sqrt{(4n\delta Z/p)} \tag{9}$$

The determination of the optimum values for $\lambda_c$ and δ are based upon the requirements for the application, for example, wavelength and imaging depth.

Further definition of the design parameters can be obtained by relating the image size to the detector pixel size in order to determine the spectrometer focal length required. Assuming a collimated beam input to the grating the diffraction limited spot size can be represented by the following expression set out in equation 10:

$$D = 1.22\lambda_c(f/d)/2 \tag{10}$$

Where f is the focal length of the spectrometer imaging optics and d is typically the lens aperture diameter which in this case is equivalent to the spectrometer input collimated beam diameter. Solving for (f/d), $$(f/d) = D/1.22\lambda_c \tag{11}$$

Therefore, given an exemplary pixel size of 10 um and setting the target diffraction limited image spot radius to the 75% of detector pixel size yields a spot diameter of 7.5 um. From equation (11) it can be determined that the ratio of the focal to input beam diameter:

$$(f/d) = 7.11 \tag{12}$$

From expression (12) for a collimated beam of 25 mm in diameter the required focal length of the spectrometer imaging optics is 178 mm. Conversely, setting the focal length to 100 mm requires a 14 mm collimated beam input. The determination of which parameter to solve for is based on other physical design constraints of the spectrometer. Further definition of the spectrometer optical design to achieve a diffraction limited spot across a detector array is known and therefore will not be discussed herein.

Using the grating equation (13):

$$\lambda_c f = \sin\theta_i + \sin\theta_d \tag{13}$$

Where
$\lambda_c$ = source center wavelength
f = spatial frequency of the grating
$\theta_i$ = angle of incidence
$\theta_d$ = angle of diffraction For standard planar transmission VPH grating designs $\theta_i = \theta_d$. Solving for f, equation (13) is reduced to:

$$f = 2\sin\theta/\lambda_c \tag{14}$$

With the practical upper limit established by:

$$f = 2/\lambda_c \tag{15}$$

Since the spectral dispersion of the VPH grating is proportional to the grating spatial frequency, design optimization is directed toward the spatial frequency. The optical design of the spectrometer is important in selecting the grating dispersion value. With a spectrometer detector array of predetermined physical length and a fixed center wavelength and bandwidth, the dispersion is selected to insure full coverage of the spectral bandwidth across the detector array.

By definition, the dispersion of the grating is the rate of change of the angle of diffraction with wavelength for a fixed angle of incidence or $\Delta\theta/\Delta\lambda$ which from a differentiation of equation (14) yields:

$$\Delta\theta/\Delta\lambda = f/\cos\theta \tag{16}$$

The optical design of the spectrometer and grating dispersion are interrelated. For a given array length and focal length of the imaging optics the angle of dispersion can be given as:

$$\phi = 2\tan^{-1}(A/2f) \tag{17}$$

where f is the focal length of the imaging optics and A is the detector array length. From equation (17) the grating dispersion relates the dispersion angle by:

$$\phi = af\delta/\cos\theta = 2\tan^{-1}(A/2f) \tag{18}$$

where a is the unit conversion from radians/mm to degrees/nm and f is determined by the detector pixel size as stated in equation (12).

Using equation (14) the expression can be reduced as follows $$(a\delta/\lambda_c)\tan\theta = \tan^{-1}(A/2f) \tag{19}$$

Solving for θ:

$$\theta = \tan^{-1}[(\lambda_c/a\delta)\tan^{-1}(A/2f)] \tag{20}$$

From the above equations, the required dispersion angle can be calculated for a given spectrometer layout. The parameters required as inputs to the equations are the detector pixel size which defines the required focal length, (A) the linear dimension of the detector array, ($\lambda_c$) the center wavelength of the source and (δ), the bandwidth of the source. From the calculated dispersion value, the grating frequency and grating angle can be calculated resulting in a complete characterization of the spectrometer design.

Grating-based spectrometer designs as discussed above disperse the light linearly as a function of wavelength across the detector array. In Fourier Transform Spectroscopy and Fourier Domain Optical Coherence Tomography, the signal of interest is the Fourier transform of the detected spectrum. The Fourier transform analog to spatial position is spatial frequency, but the detector captures spatial period and thus requires an additional interpolation step to scale the detected spectrum from spatial period to spatial frequency. This resampling is a time-consuming process, and the elimination of such would enable both faster processing and more accurate sampling in spatial frequency or wavenumber (k) space.

Additionally, resampling is inadequate to the task of providing a constant depth scale in the Fourier transformed spatial image. The chirped sampling (relative to the spatial frequency) yields a chirp in depth per pixel across the image depth. As the imaging window becomes deeper, this chirp is more deleterious to dispersion compensation and to quantitative measurements across the image depth. It is therefore desirable to design an FDOCT system sampled linearly in frequency (k, wavenumber).

As indicated, the maximum depth of the SDOCT system is defined by the spatial sampling of the spectrum at the detector—increased wavelength (or wavenumber) sample density allows for sampling of higher frequency fringes on the spectrum and thus returns signals from deeper depths. This relationship is related by:

$$Z_{max} = \frac{1}{4*\delta v_s} \tag{21}$$

Where $\delta v_s$ is the wavenumber sampling at the detector.
Wavelength and wavenumber are related by:

$$\frac{\Delta v}{v} = \frac{\Delta\lambda}{\lambda} \tag{22}$$

Equi-sampling in wavenumber will reduce the burden on computational resampling, and improve the linearity of the depth scaling in the final image. Additionally, application of wavenumber or k-linearization is well suited to channelized imaging, for example through the use of a comb filter for SDOCT and SSOCT, or through the use of controlled duty-cycle sampling in SSOCT, as discussed below.

Design of k-linearized spectrometers using a prism air-spaced with respect to a grating has been reviewed elsewhere, for example, in *Fourier Domain optical coherence tomography with a linear-in-wavenumber spectrometer* by Hu et al. However, the use of a prism-air space-grating configuration requires control of extra degrees of freedom, and adds to the number of glass-air interfaces, potentially reducing manufacturability and increasing costs. As originally described in *Constant-dispersion grism spectrometer for channeled spectra* by Traub, a prism-grating (GRISM) structure in intimate contact may be adequate to the task of creating, in the language of Traub, a constant dispersion (k-linear) spectrograph. Traub, however, does not provide a prescription for practical design of a grism spectrometer that meets the requirements of FDOCT imaging, including the relationship between required dispersion and degree of linearization required. As shown below, with proper specification of grating spatial frequency, prism index and chromatic dispersion, prism angle, and input angle, a k-linear spectrometer can be designed with sufficient linearity to support a frequency-channelized implementation with improved sensitivity falloff characteristics.

The exit angle, $\beta$, of an isosceles prism is related to the entrance angle, $\alpha$, the vertex angle, $\epsilon$, and the index of refraction of the prism as a function of wavelength, $n_p(\lambda)$. Using Snell's law and assuming the medium surrounding the prism is air, the angle of the light after refracting at the first surface of the prism, $\theta_1$, is:

$$\theta_1 = \sin^{-1}\left(\frac{1}{n_p(\lambda)}\sin\left(\alpha - \frac{\epsilon}{2}\right)\right) \quad (23)$$

Following the same logic, the angle after refraction at the second surface of the prism, $\theta_2$, is:

$$\theta_2 = \sin^{-1}\left(\frac{n_p(\lambda)}{n_g(\lambda)}\sin\left(\theta_1 \frac{\epsilon}{2}\right)\right) \quad (24)$$

Where $n_p(\lambda)$ is the wavelength dependent index of refraction of the grating.

The grating equation is:

$$\sin\alpha + \sin\beta = \frac{-m\lambda}{d} \quad (25)$$

Where $\alpha$ is the angle of incidence onto the grating, $\beta$ is the exit angle of the grating, m is the diffraction order, $\lambda$ is the wavelength of the incident light, and d is the groove spacing. Rearranging for the exit angle yields:

$$\beta = \sin^{-1}\left(\frac{-m\lambda}{d} - \sin\alpha\right) \quad (26)$$

For a fixed input angle, in the small angle approximation, the angular change as a function of wavelength is:

$$\frac{d\beta}{d\lambda} = \frac{-m}{d} \quad (27)$$

Wavenumber, $\nu$, is:

$$\nu = \frac{1}{\lambda} = \frac{k}{2\pi} \quad (28)$$

Converting the dispersion equation to wavenumber, $\nu$, yields:

$$\frac{d\beta}{d\nu} = \frac{-m}{\nu^2 d} \quad (29)$$

The Sellmeier equation relates the index of refraction $n(\lambda)$ to the wavelength of light using well-characterized, commonly known coefficients, B1-3 and C1-3:

$$n(\lambda) = 1 + \frac{B_1\lambda^2}{\lambda^2 - C_1} + \frac{B_2\lambda^2}{\lambda^2 - C_2} + \frac{B_3\lambda^2}{\lambda^2 - C_3} \quad (30)$$

Equation 30 in terms of wavenumber is:

$$n(\nu) = 1 + \frac{B_1}{1 - \nu^2 C_1} + \frac{B_2}{1 - \nu^2 C_2} + \frac{B_3}{1 - \nu^2 C_3} \quad (31)$$

This equation can be used to model the index across the wavelengths or wavenumbers for a given SDOCT wavelength range.

Figure 7:
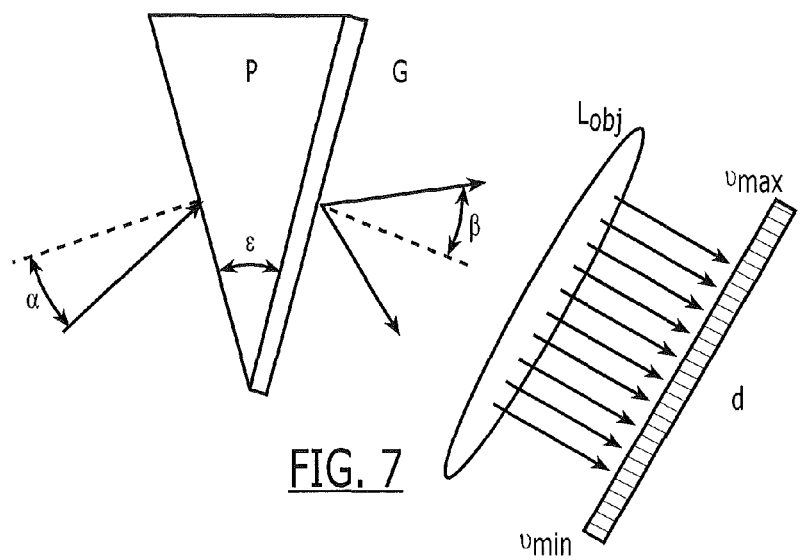
FIG. 7 is a block diagram illustrating a GRISM in accordance with some embodiments of the present inventive concept.

A k-linear GRISM is a combination of a prism and a grating in which the wavenumber dispersion of the prism balances the wavenumber dispersion of the grating. This can be tailored to yield approximately constant wavenumber dispersion across the output of the GRISM. One implementation of this design uses an isosceles prism with a flush-mounted VPH grating as illustrated in FIG. 7 of the present application. Alternative designs that reverse the order of grating and prism, or that utilize prisms on both the entrance face and exit face of the gratings may be employed without deviating from the invention. Note also that a chirped holographic grating can be tailored to replicate the transmission function of generally any GRISM. For example, a chirped grating holographically written will perform as the equivalent GRISM, without the need for mounting a physical GRISM to the grating in the spectrometer. The concept of chirped gratings are discussed in, for example, U.S. Pat. Nos. 4,834,474 and 7,224,867. Techniques for designing a transfer function and preparing a holographic transmission filter to provide the targeted transfer function are discussed in, for example, U.S. Pat. No. 7,519,248. These concepts have not previously been applied to k-linearized spectrometers.

In particular, as illustrated in FIG. 7, P and G are the prism and grating, respectively. $\epsilon$ is the vertex angle of the prism, $\alpha$ is the angle of incidence onto the prism and $\beta$ is the deflection angle from the GRISM. As illustrated, d is the width of the detector, for example, 20.48 mm. The objective lens $L_{obj}$ represents the optics used to focus the GRISM output across the detector array. $v_{min}$ and $v_{max}$ are the wavenumber range minimum and maximum values, respectively.

Figure 8:
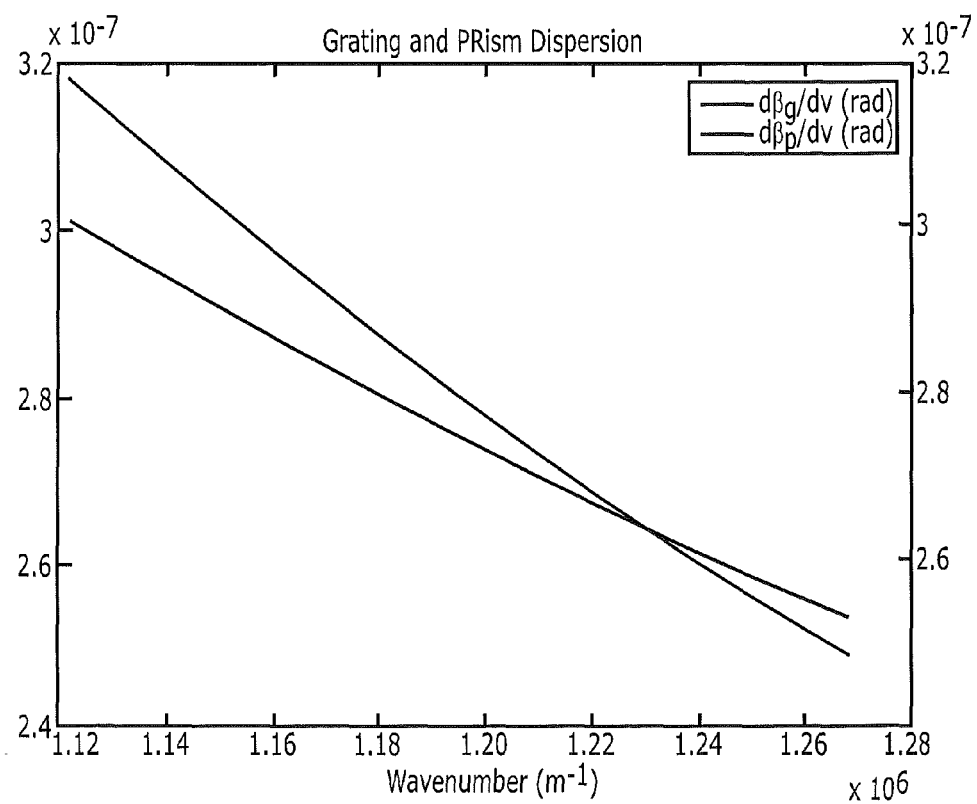
FIG. 8 is a graph illustrating grating and prism dispersion in accordance with some embodiments of the present inventive concept.
Figure 9:
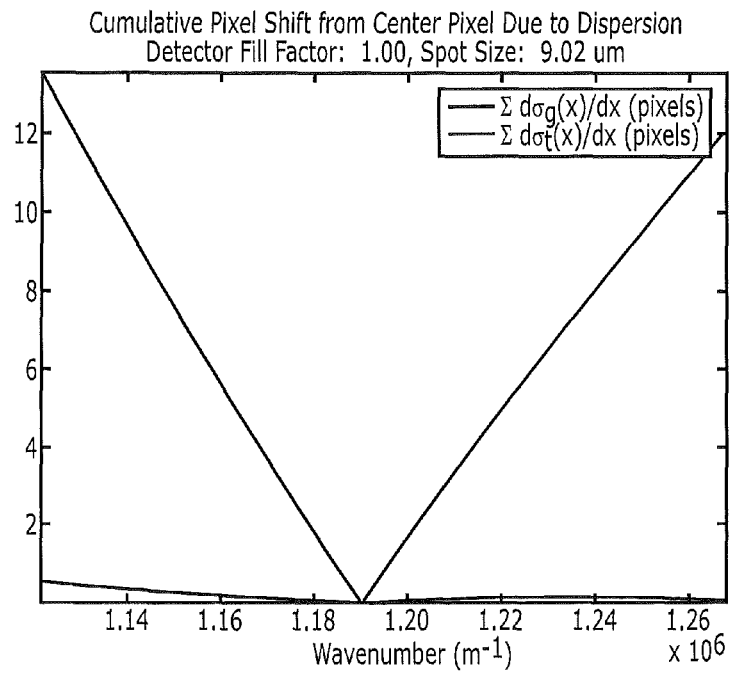
FIG. 9 is a graph illustrating cumulative wavenumber sampling shift as a cumulative error in channel position from pixel position, as referenced to the center pixel, due to dispersion in accordance with some embodiments of the inventive concept.
Figure 10:
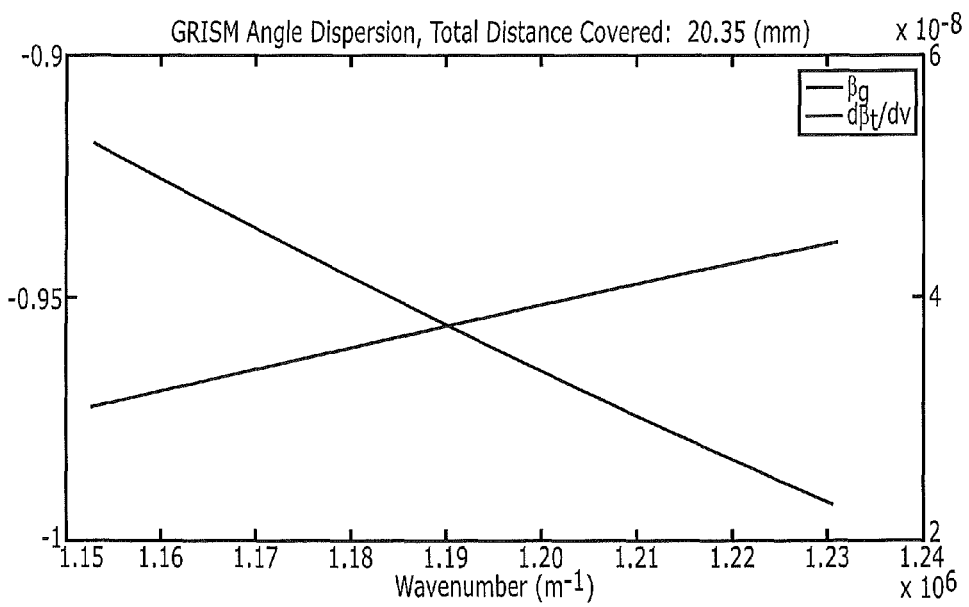
FIG. 10 is a graph illustrating GRISM angle dispersion in accordance with some embodiments of the present inventive concept.

FIG. 8 is a graph illustrating grating and prism dispersion in accordance with some embodiments of the present inventive concept. The dispersions of grating and prism are additive, such that the utilization of a prism reduces the dispersive power required of the grating. FIG. 9 is a graph illustrating cumulative pixel shift from center pixel due to dispersion in accordance with some embodiments of the inventive concept. A non-linearized spectrometer will not support a fully frequency-channelized set of spectral elements whereas a k-linear spectrometer can be channelized such that the cumulative offset of the Nth frequency channel from the Nth detector pixel is less than one pixel, and preferably less than one-half pixel. FIG. 10 is a graph illustrating GRISM angle dispersion in accordance with some embodiments of the present inventive concept, demonstrating the linearity with respect to wavenumber.

Non-ideal spectral sampling in FDOCT systems imposes a depth-dependent falloff of Signal-to-Noise Ratio (SNR). This falloff is based on the lineshape of the sampled element. For example, if the detected sampling function is a square pixel (rect function), then the transform of the sampling function is a sync function, and the shape of the sync function defines the falloff window.

Sensitivity falloff is in effect a characteristic of the finite coherence length of each sampled spectral element. In principle, sampling a comb of single frequencies, for example, a comb of delta functions, would completely eliminate sensitivity falloff. This is not achievable in practice. However, a comb convolved with a function, for example a Gaussian or Lorentzian, whose width is less than the comb spacing will demonstrably improve the falloff characteristics; the narrower the convolving function, or stated alternatively the smaller the duty cycle of the comb, the greater the positive impact on sensitivity falloff. This effect will be operative for any implementation of FDOCT, whether SDOCT or SSOCT, and whether applied with a resampled wavelength-sampled spectrum or a k-linear sampled spectrum, though operation in conjunction with a k-linear sampling, such that each sampled element records a spectral element of the comb, may be preferred.

A Fabry-Perot etalon can be used to provide such a comb source. A practical etalon may be composed of a glass block with 2 partially reflecting surfaces. As will be described, the two key attributes of the etalon are the free spectral range (FSR) and the Finesse. The FSR determines the sampling interval, which in some embodiments is designed to match the desired sampling interval, for example, the pixel spacing of the k-linear spectrometer or the k-trigger of the SSOCT light source. The FSR is closely related to the optical path length through the etalon. The Finesse sets the spectral width at each output frequency, or the duty cycle of the etalon transmission function. The Finesse is closely related to the reflectivity of the interfaces of the etalon.

Light incident etalon, normal to the surface or angled, will either pass through block or reflect from the block (assuming a lossless etalon interior). Transmission through the block is defined by:

$$T_e = \frac{T^2}{1-R^2}\left(\frac{\sinh\gamma}{\cosh\gamma - \cos\delta}\right) \quad (32)$$

Where T and R are the surface transmission and reflection values, $\gamma = \ln(1/R)$, and $\delta$, the phase of the light traveling through the block, is defined by:

$$\delta = \frac{4\pi}{\lambda} nl\cos\theta \quad (33)$$

Where n is the index of refraction of the glass block, $\lambda$ is the wavelength of the incident light, l is the thickness of the block, and $\theta$ □ is the angle of incidence onto the block.

The Free Spectral Range (FSR) of the etalon defines the spacing between adjacent transmission peaks and is defined by:

$$FSR = \frac{\lambda_0^2}{2nl\cos\theta + \lambda_0} \quad (34)$$

Where $\lambda_0$ is the center wavelength of the transmission peak. The Full Width at Half Maximum (FWHM or $\Delta\lambda$) of each transmission peak is related to the finesse, $\mathcal{F}$, of the etalon by:

$$\mathcal{F} = \frac{FSR}{\Delta\lambda} = \frac{\pi}{2\arcsin(1/\sqrt{F})} \quad (35)$$

Where F is the coefficient of finesse, which is defined by:

$$F = \frac{4R}{1-R^2} \quad (36)$$

The thickness of the block and the reflectivity of the surfaces can be tailored to provide a comb source for a given wavelength range that provides a sub-interval lineshape and a FSR equal to the spectral sampling interval.

Figure 23:
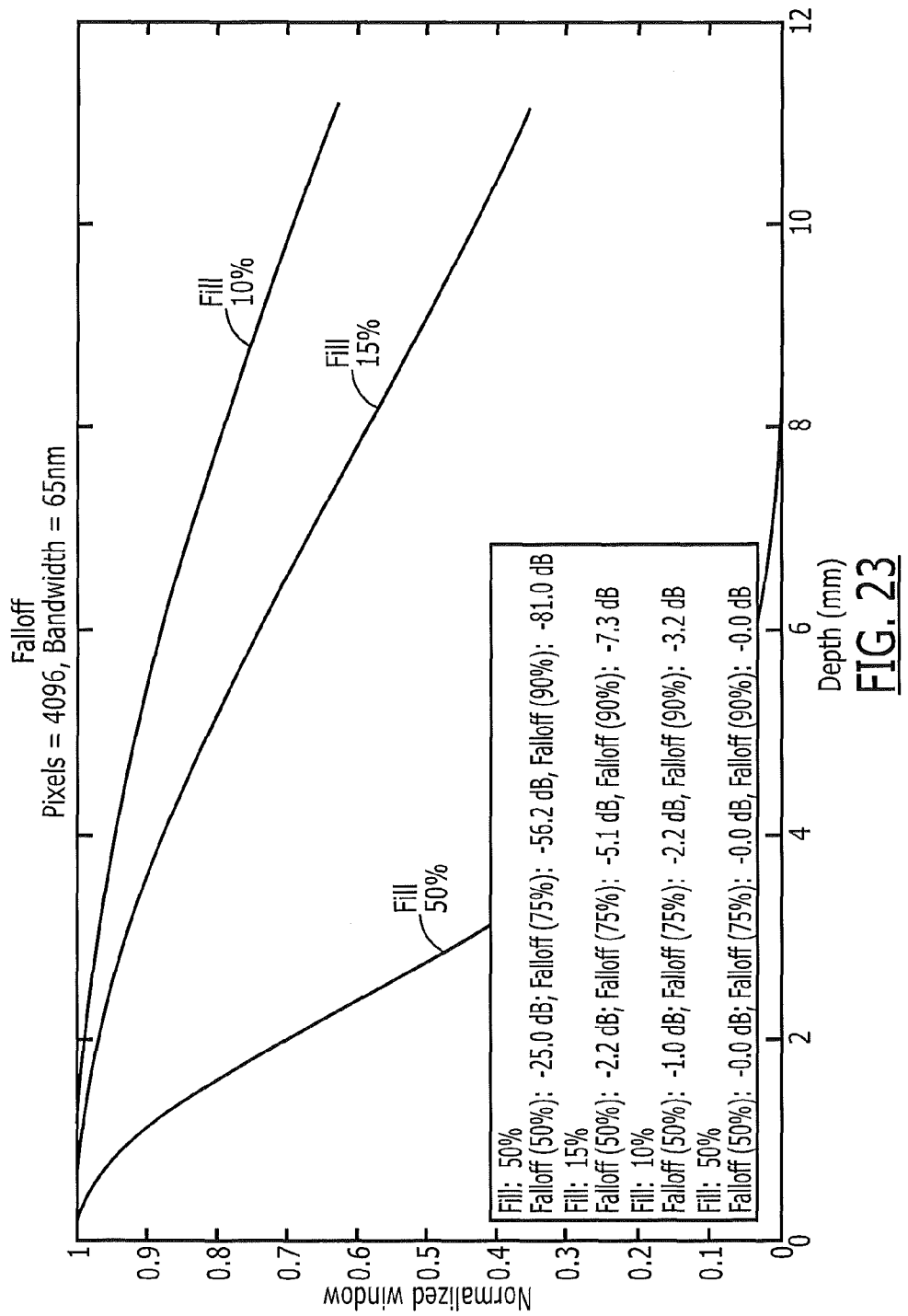

The maximum depth of a spectrometer is defined by the frequency spacing at the detector; finer frequency sampling yields a deeper maximum depth. 56 nm from 812-868 nm dispersed across 2048 pixels will provide a spectral sampling of 0.027 nm/pixel and a maximum depth of 6.55 mm. Assuming an incident angle of $\pi/8$ (22.5°) and an index of refraction of the etalon glass of 1.55, the FSR and FWHM can be tailored to provide sub-pixel FWHM and transmission peak spacing equal to the spectral sampling interval. Assuming a GRISM-based, constant wavenumber dispersion spectrometer is in place, the spectral sampling will be evenly spaced from $1.15\times10^6$ m$^{-1}$ to $1.23\times10^6$ m$^{-1}$. Reflectivity R of 0.24 yields a finesse of 1.1, and for a thickness of 10 mm, this yields a mean FSR of 0.024 nm and a FWHM of 0.021 nm (FIG. 1). Increasing the finesse shortens the FWHM as illustrated below in FIG. 21 and subsequently the falloff effect as illustrated in FIG. 23, but this also decreases the total power output of the source.

For comprehensive FDOCT imaging of the eye by rapidly switching between imaging modes designed for imaging different ocular structures along the visual axis, it would be desirable for the imaging depth (axial field of view) of each mode to be optimized for the expected length and desired axial sampling density of each structure. For example, for imaging of the entire anterior segment, the optimal imaging depth is the expected maximum anterior segment depth of the anticipated patient population, which may be 6 to 8 millimeters. For imaging of the retina, which is less than about 1.0 mm thick in most locations and contains many closely spaced layers and structures, it may be preferable for the retinal imaging mode to have a shorter imaging depth and denser axial sampling.

In all FDOCT systems, as has been expressed, there is an inverse relationship between the imaging depth $z_{max}$ and the spectral sampling interval in wavenumber units $\delta_s k$ given by:

$$z_{max} = \frac{\pi}{2 \cdot \delta_s k} \quad (37)$$

The total sampled spectral width is given by the spectral sampling interval $\delta_s k$ multiplied by the number of spectral samples acquired per A-scan, typically several thousand, and thus the depth sampling density is given by the imaging depth divided by the number of spectral samples, or some multiple of that number if interpolation is performed. In SDOCT systems, the spectral sampling interval $\delta_s k$ is typically fixed by the spacing of the pixels on the array detector used in the spectrometer and the magnification and spectral dispersion of the internal optical elements of the spectrometer. In SSOCT systems, however, the spectral sampling interval $\delta_s k$ is determined by the sweep rate of the light source and/or the electronic sampling rate of the analog to digital converter which is recording the SSOCT signal, at least one of which may be rapidly adjustable electronically or by other means. In the case of SSOCT, therefore, it will be desirable to adjust the spectral sampling interval and thus the imaging depth and depth sampling density (according to the prescription in equation 3) on the fly according to the structure or part of the eye which is being imaged. This imaging depth switching may be coupled to sample and reference arm mode switching, such that when switching the sample arm optics and reference arm delay from the anterior segment to the retina, for example, the imaging depth is also switched to allow for optimal imaging depth and sampling density of retinal structures. Or, the imaging depth and depth sampling density may be varied within a single operating mode of the sample and reference arm optics, for example to switch between short imaging depth, high spatial sampling density imaging of the cornea and long imaging depth, lower spatial sampling density imaging of the entire anterior segment.

In unmodified SDOCT systems, $\delta_s k$ is usually limited by the spectral resolution of the spectrometer including the finite spacing of the CCD pixels and diffraction in the spectrometer. In unaltered SSOCT systems, $\delta_s k$ is typically limited by the instantaneous lineshape of the swept laser source, although other factors such as the bandwidth of the detection electronics may also come into play.

In comprehensive ocular SSOCT systems as described above wherein the spectral sampling interval and depth sampling density are adjusted as per equation 3 according to the structure or part of the eye which is being imaged, it is desirable to further implement a comb filter for decreasing the extent of sensitivity falloff which is also suitably adjustable to maintain the comb spacing or FSR as the spectral sampling interval is adjusted. In Fabry-Perot etalons, the FSR is related to the thickness of the etalon, the index of refraction of the material inside the etalon, and the angle of light incidence upon the etalon. According to some embodiments, one or more of these parameters should be varied in synchrony with changing the spectral sampling interval $\delta_s k$ in order to keep the comb filter peaks within their respective spectral sampling intervals. In some embodiments, this may be done by employing a tunable Fabry-Perot filter, for example, which utilizes a piezo-electric element to electronically tune its FSR. Electronic control of the FSR of such a filter may be electronically coupled to the mechanism for changing the spectral sampling interval $\delta_s k$, for example by changing the digitization rate of the analog-to-digital converter.

Note that in such a case the FSR of the comb filter matches the sampling rate of the detector. This is the function of k-triggers commonly deployed in SSOCT systems to trigger the acquisition of spectral elements. Thus it is conceivable to use the comb filter for a secondary function, to act as the system k-trigger. The converse property does not hold. In particular, a k-trigger is not implemented in current systems to operate as a comb source generator for the SSOCT system. The proposed comb filter may be used as a k-trigger in at least two different modes. In a first mode, a small fraction of the transmissive (T) output of the comb filter is split out of the source path to k-trigger circuitry. In such a configuration, the k-trigger implementation is directly analogous to implementations currently used in the art, with the benefit that a separate device is not required. This mode is fully functional, but comes at some cost to the power available for imaging.

Figure 24:
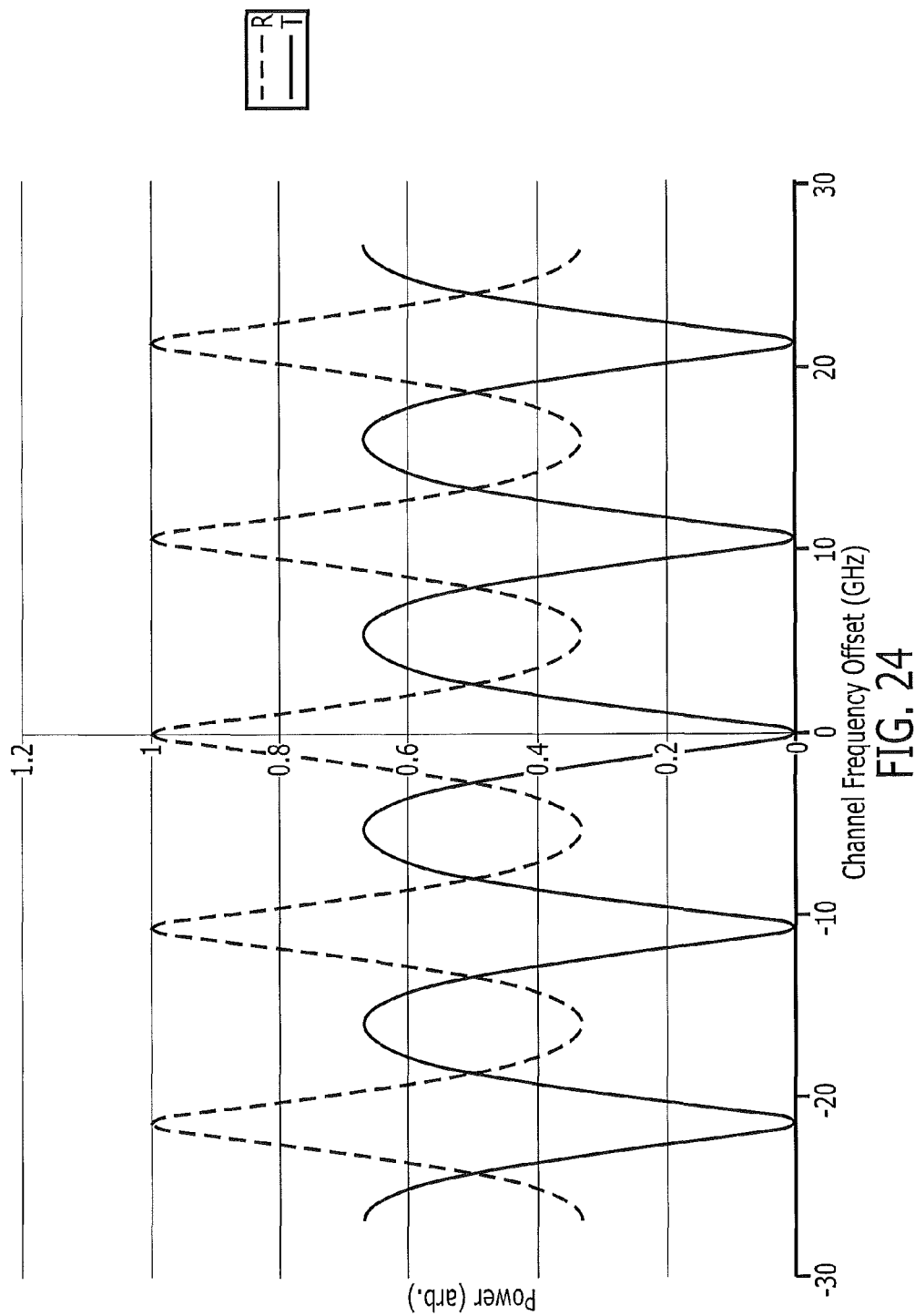

A second mode is to use the back-reflected (R) light from the filter. The backreflection from a lossless etalon filter is the spectral complement to the transmission through the filter, as illustrated in FIG. 24. This backreflection may be used as the k-trigger for an SSOCT system. Embodiments illustrating the second mode including a swept source followed an optical isolator, an etalon filter, and an optical circulator, will be discussed further below with respect to FIG. 19. The backreflected output from the etalon is directed to k-trigger circuitry and applied to trigger spectral sampling of a balanced heterodyne detector. The balanced detector sees interference signature both from the detector port of the coupler, and the shunt port of the optical circulator.

To resolve the complex conjugate artifact, several academic groups have pointed out that a second spectral interferogram may be obtained with the phase offset $\phi$ in shifted in phase by $\pi/2$. Combining the real and imaginary parts yields the complex interferometric signal $\hat{D}_i[k_m] = \hat{D}_i^0[k_m] + j\hat{D}_i^{90}[k_m]$, the Fourier transform of which reveals an A-scan with the position of the sample arm reflector unambiguously determined. A method to obtain the complex signal using only two phase stepped scans has been demonstrated, but completely artifact-free tissue imaging has only been demonstrated using a 5 step algorithm in which the additional phase steps were necessary to compensate for phase errors.

Figure 11:
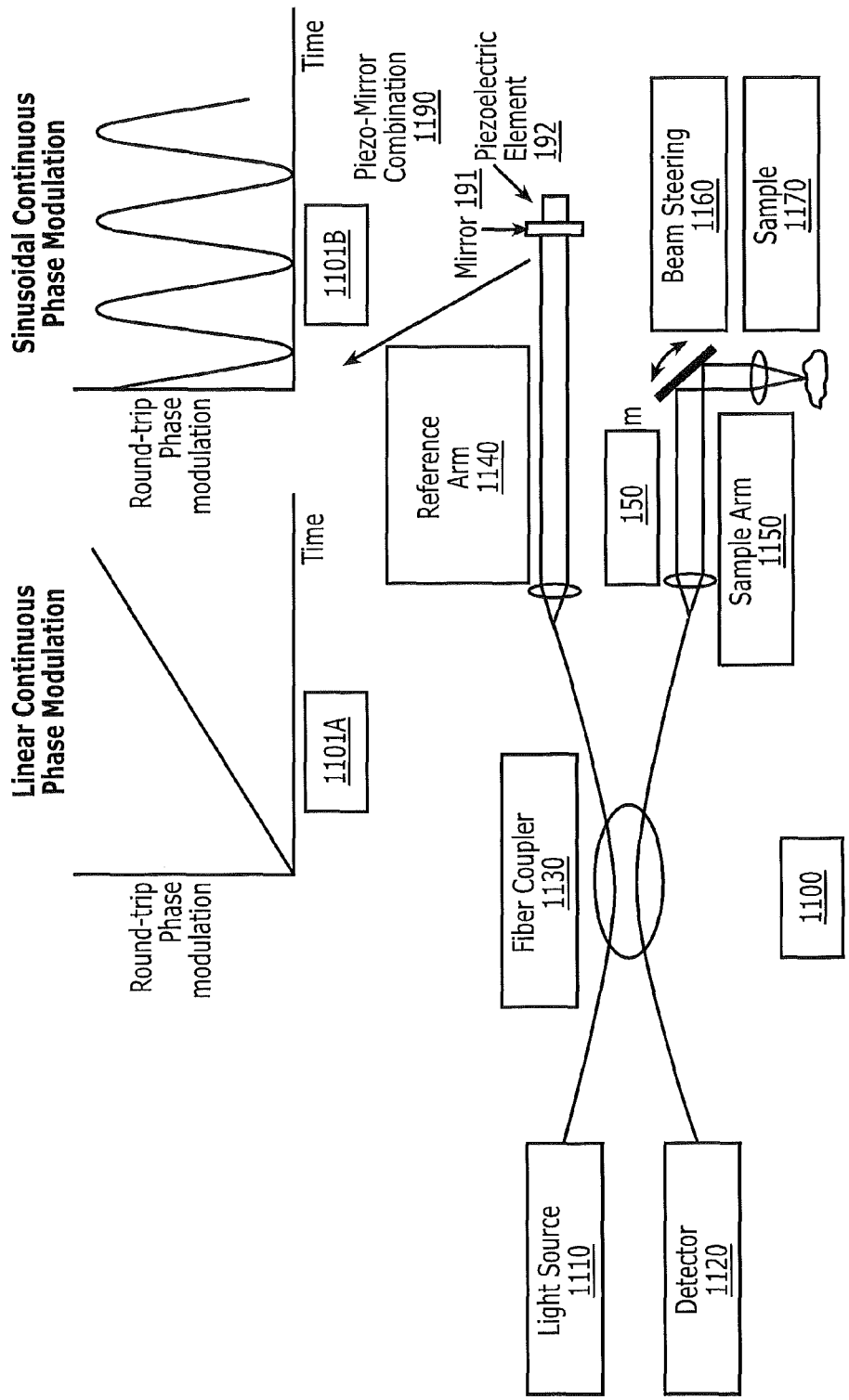
FIG. 11 is a schematic block diagram illustrating an optical coherence tomography (OCT) system including a piezoelectric transducer (PZT) element in accordance with some embodiments of the present invention.

For an SDOCT system embodiments for complex conjugate removal (CCR) may be via sinusioidal phase modulation as discussed in, for example, commonly assigned U.S. Pat. No. 7,742,174, the disclosure of which has been incorporated herein above. In particular, the system discussed in accordance with some embodiments of U.S. Pat. No. 7,742,174 is illustrated in FIG. 11. Referring to FIG. 11, the optical coherence tomography (OCT) system 1100 includes a piezoelectric transducer (PZT) element. As illustrated in FIG. 11, the system 1100 further includes a light source 1110, a detector 1120, a fiber coupler 1130, a reference delay 1140, a piezomirror combination 1190, a beam steering unit 1160, a sample arm 1150 and a sample 1170. The light source 1110 may include a broadband light source and the detector 1120 includes a spectrometer illuminating a multichannel detector, such as a linear charge-coupled device (CCD) array. A piezomirror combination 1190 is located in the reference arm 1140 of the interferometer, which may include a mirror 1191 and a piezoelectric element 1192 as illustrated therein.

As discussed in U.S. Pat. No. 7,742,174, phase modulation involves placement of a path length modulation in either the sample or reference arm of an SDOCT system which varies the differential path length between the arms with amplitude and phase given in the text preceding equation (14) in U.S. Pat. No. 7,742,174, at a rate corresponding to π/4 radians of phase modulation per A-scan integration time of the spectrometer. Then, each set of four sequential A-scan acquisitions are combined according to equation (14) of U.S. Pat. No. 7,742,174 in order to generate an A-scan with total depth equal to $2*z_{max}$ as defined above. If the amplitude, phase and frequency of the modulation are set as specified in U.S. Pat. No. 7,742,174, then the resulting A-scan should theoretically be completely free of DC, autocorrelation, and complex conjugate artifacts.

However, slight deviations from perfection in achieving these parameters such as will be experienced in any real physical implementation of sinusoidal phase modulation may lead to a degradation of performance compared to the ideal result in the form of incomplete complex conjugate artifact suppression. Thus, an additional step of applying quadrature projection processing as discussed with respect to FIG. 2 of U.S. Patent Application Publication No. 2008/0170219 may be applied to improve the complex conjugate artifact rejection, at the cost of a small amount of reduced signal to noise ratio. Quadrature projection processing is an algorithmic step which does not require any hardware modification and which reduces the complex conjugate artifact from imperfectly phase modulated SDOCT data by forcing the real and imaginary parts of the recorded A-scan signal to be orthogonal.

For an SSOCT system, some embodiments remove complex conjugate removal (CCR) using the heterodyne CCR method as discussed in commonly assigned U.S. Pat. No. 7,336,366, which involves introducing a frequency shift between the sample and reference arm light and thus shifting the carrier frequency of the image-bearing signal away from DC, about which the complex conjugate artifact is centered. With the addition of this frequency shift, the A-scan free of complex conjugate artifact is found from the Fourier transform of the detected signal, centered at the frequency shift value. If an A/D converter is used which has much higher bandwidth than the SSOCT signal itself, then the frequency shift value can be set to be many times the frequency encoding the $z_{max}$ value of the A-scan, thus the complex conjugate artifact will be located far in frequency space away from the A-scan data. If a very high sweep speed is used, however, such that the SSOCT signal already occupies a substantial fraction of the A/D converter bandwidth, then the complex conjugate artifact may only be shifted to the borders of the depth-doubled A-scan. This method of heterodyne CCR is consistent and will not interfere with the embodiments described above for filtering to improve sensitivity falloff and sampling to adjust maximum single-sided imaging depth.

Figure 2:
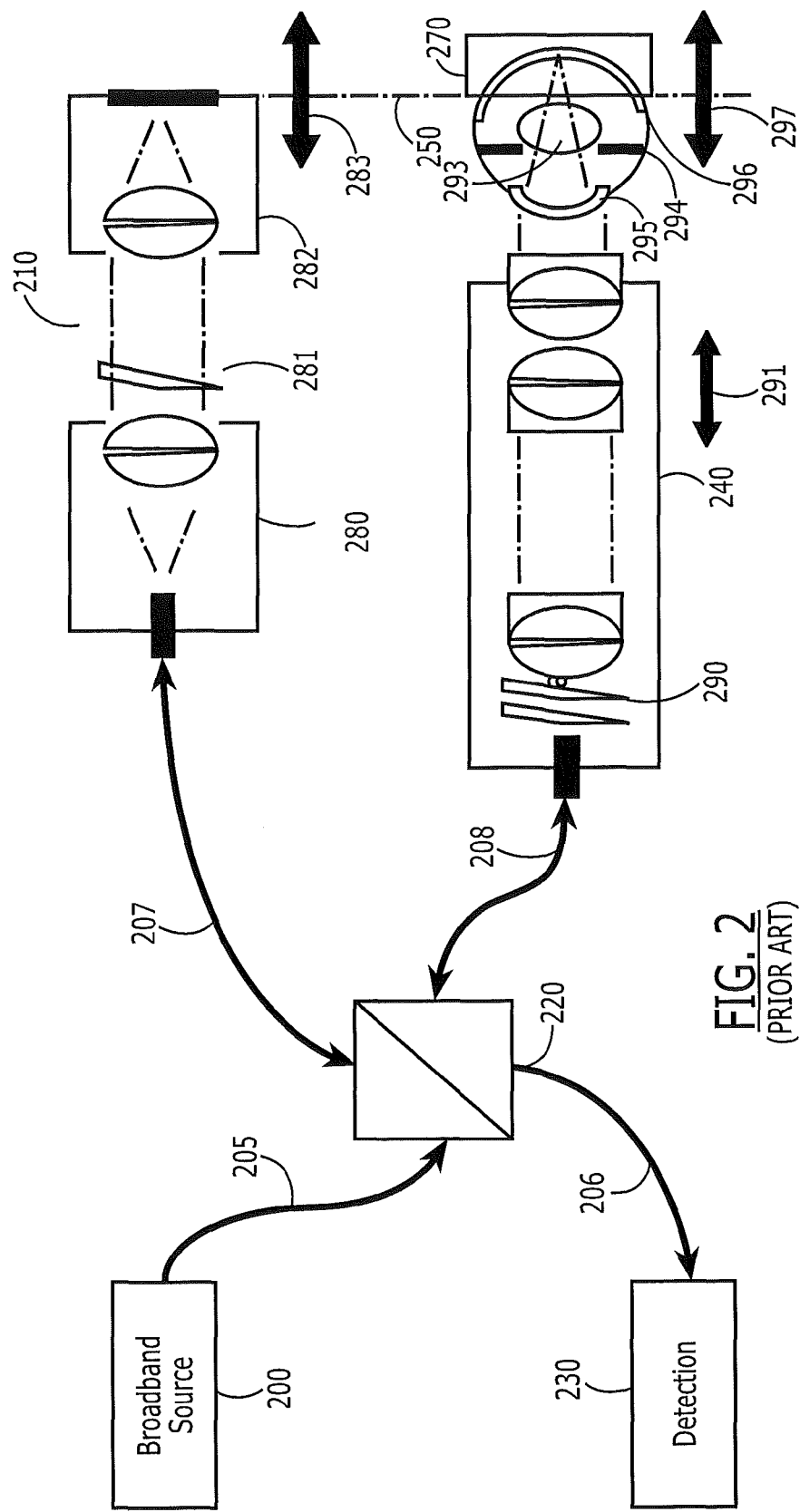
FIG. 2 is a block diagram illustrating a Fourier domain retinal optical coherence tomography system in accordance with some embodiments of the inventive concept.
Figure 3:
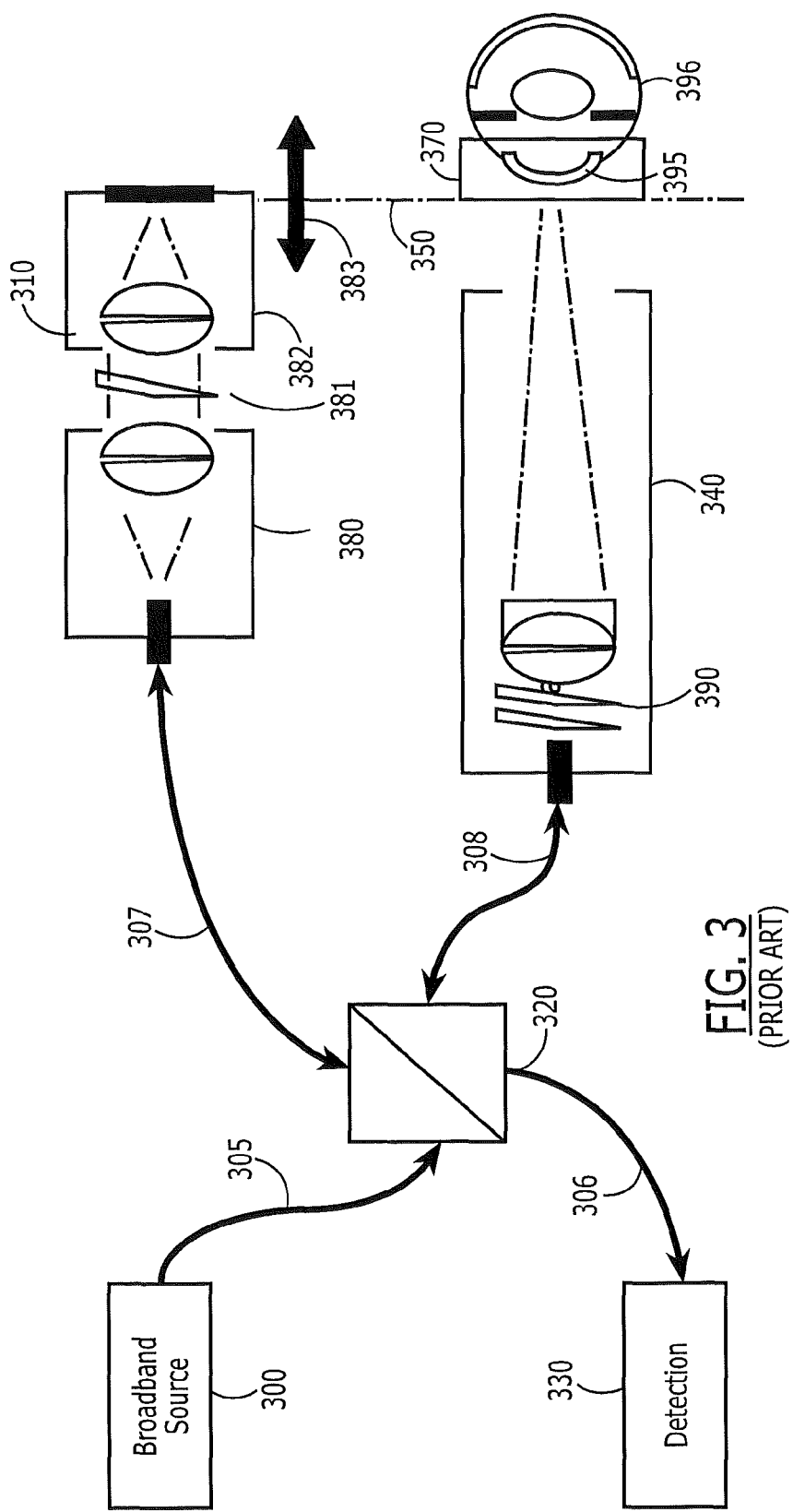
FIG. 3 is a block diagram illustrating a Fourier domain corneal optical coherence tomography system in accordance with some embodiments.

Some embodiments of the present inventive concept are directed to comprehensive volumetric imaging of all ocular structures along the visual axis using Fourier-domain optical coherence tomography (FDOCT). Current-generation FDOCT systems, including spectral-domain (SDOCT) and swept-source (SSOCT) implementations, are in routine clinical use for diagnosis of retinal pathologies. FDOCT systems have also been applied for imaging of the anterior segment of the eye. Existing optical designs for scanning the anterior segment and retina are illustrated in FIGS. 1 through 3 of the present application. FDOCT is useful for examination of the anterior segment of the eye, for diagnosis of corneal, iris, and lens pathologies as well as for quantitative biometry of the anterior segment including measurements of corneal refractive power, corneal thickness, anterior chamber depth, lens optical power, and lens thickness. These parameters resulting from anterior segment biometry, with the addition of eye length measurement, are needed for calculation of intraocular lens implant power for cataract surgery. Current methods for evaluation of these parameters are limited to measurement along a single axis, and thus provide only central values for these parameters which may not accurately account for off-axis variations and aberrations. With the ability to rapidly acquire densely sampled 2D images and 3D volumes of information, FDOCT offers the potential to perform substantially improved characterization of the refractive properties of the entire eye, if calibrated and correlated volumetric images of the anterior segment, lens, and retina could be acquired either simultaneously or in rapid succession in the same patient.

Current-generation FDOCT instruments, however, are not capable of imaging with sufficient depth field of view to record data from all of these structures with the same instrument without time-consuming interchange of optics and of the reference arm length. Thus, there is a need for FDOCT system designs capable of either simultaneous imaging of the anterior segment, lens, and retina or of rapidly switching between such modes during a rapid acquisition sequence which preserves their relative displacements in order to perform comprehensive volumetric imaging of all ocular structures along the visual axis. Such switching should preferably be rapid, on the time scale of a few A-scans acquisition time, i.e. a few milliseconds, and should allow for the maximum possible re-use of optics and mechanics in both modes to reduce total system cost and complexity.

Figure 12:
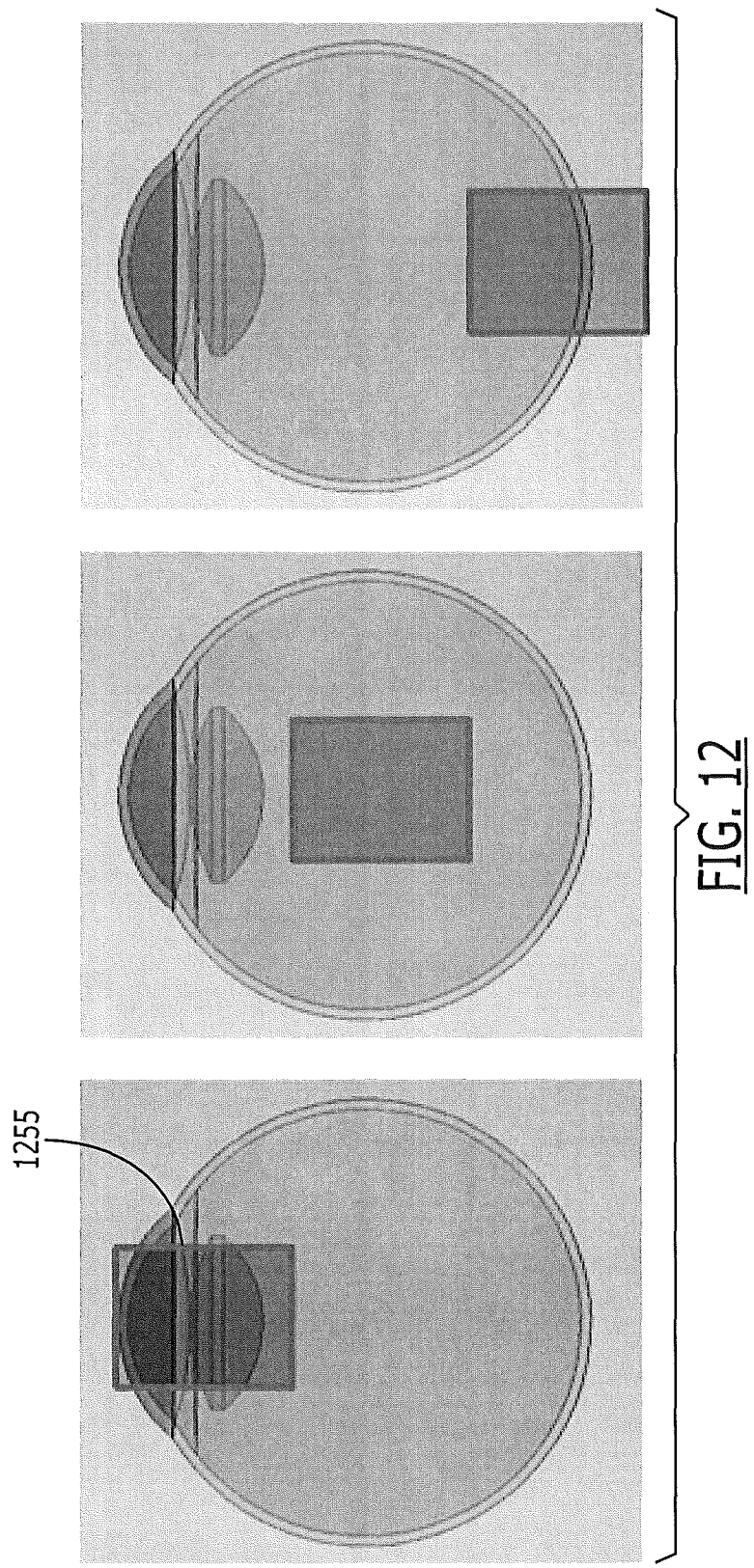
FIGS. 12 and 13 are diagrams illustrating a series of imaging windows that may be applied for a select variety of imaging circumstances in accordance with some embodiments of the inventive concept.
Figure 13:
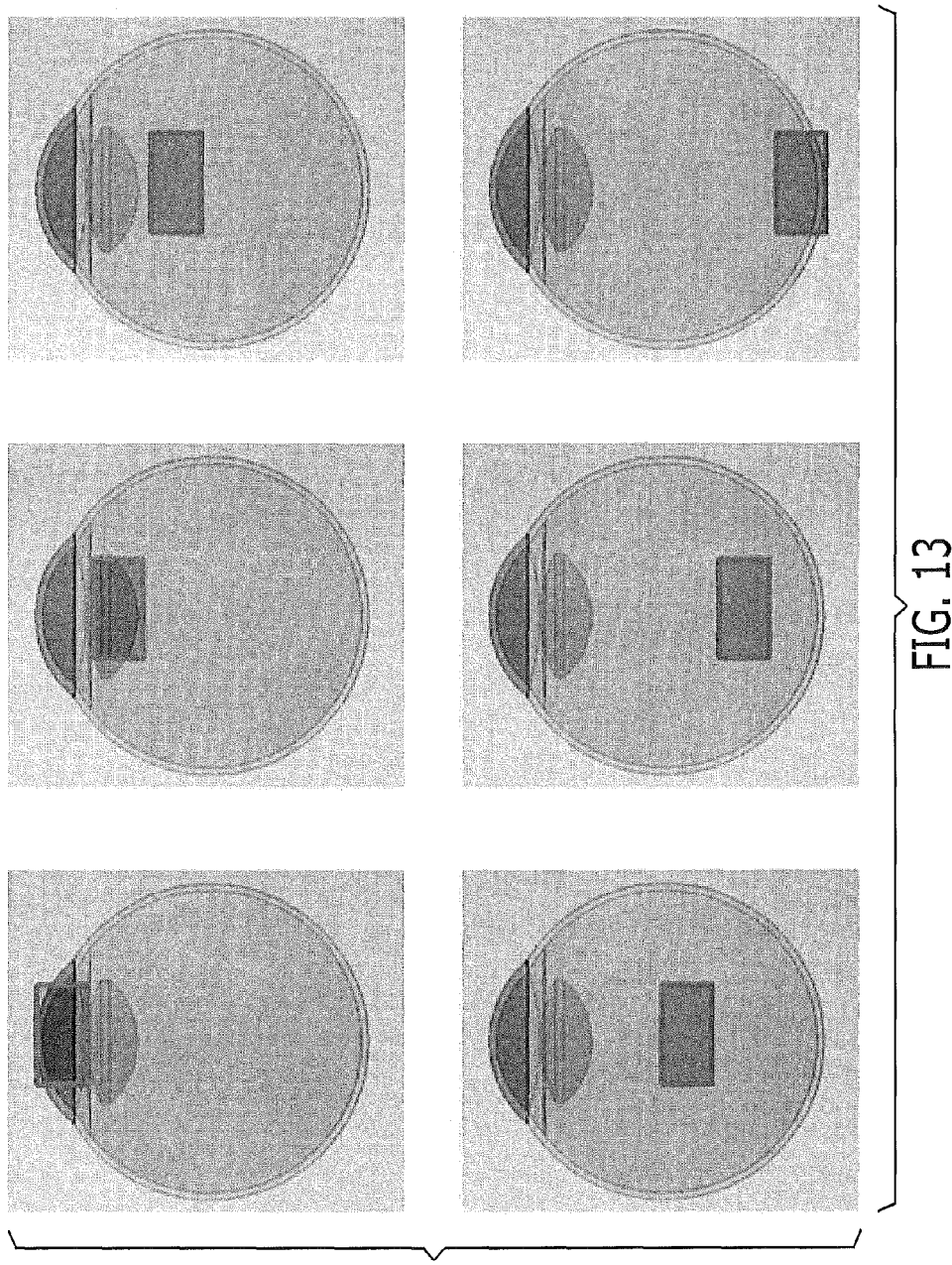

Applying the techniques described in this invention, a dynamically adjustable extended depth imaging system may be applied to ophthalmic imaging for targeted imaging of any region of the eye with optimized depth field of view and image resolution. FIGS. 12 and 13 illustrate a series of imaging windows 1255 and 1355 that may be applied for a select variety of imaging circumstances, for example, vitreoretinal surgery, cataract surgery, cornea and anterior chamber surgery and the like. As illustrated in FIGS. 12 and 13, the series of windows may have a variety of sizes, shapes and locations in accordance with embodiments discussed herein.

Figure 14:
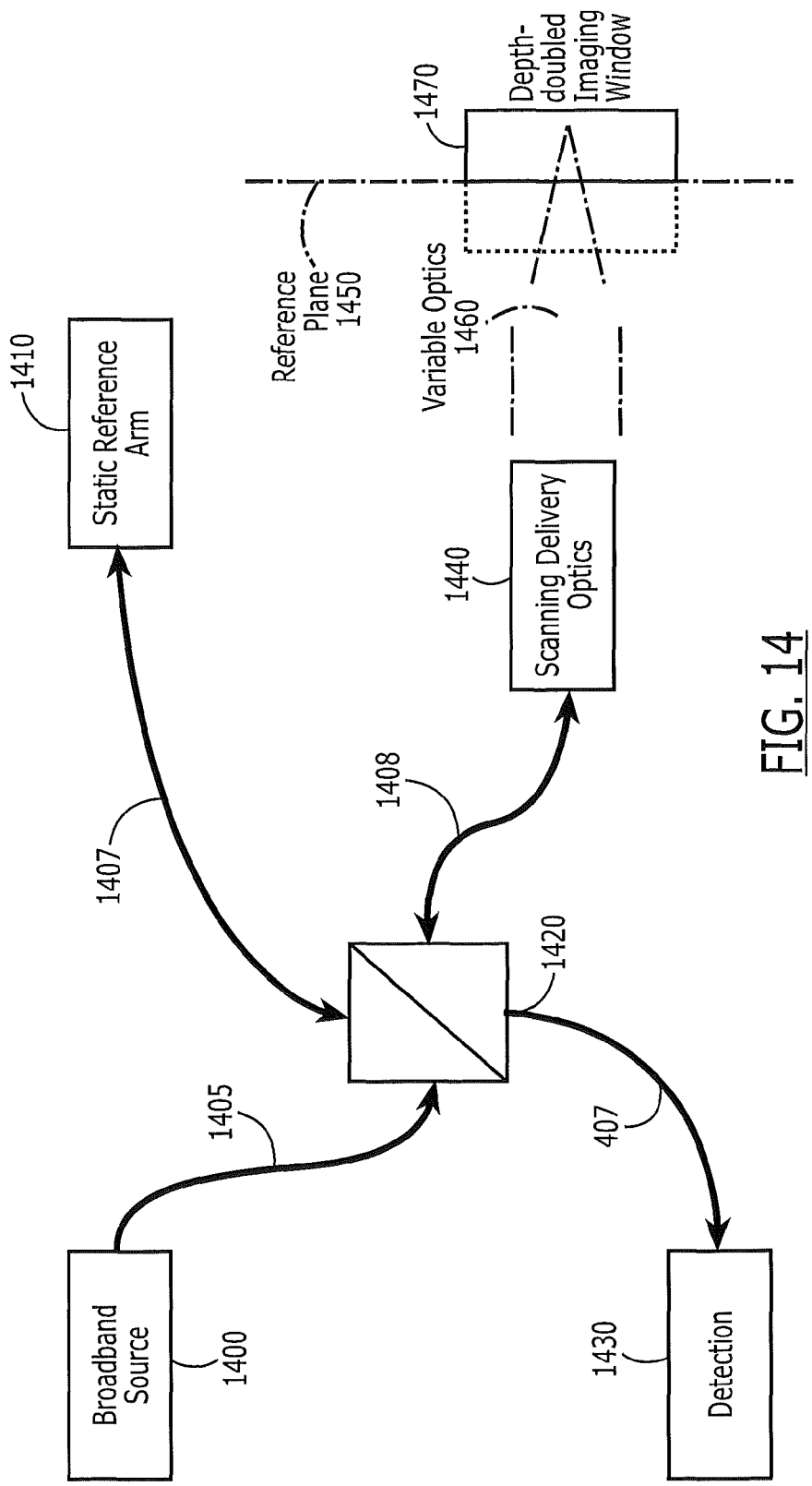
FIG. 14 is a block diagram of an extended depth fourier domain OCT imaging system in accordance with some embodiments of the inventive concept.

Referring now to FIG. 14, a block diagram illustrating an extended depth FDOCT system in accordance with some embodiments of the present invention will be discussed. As illustrated in FIG. 14, the system includes a source 1400, a reference arm 1410 and a sample arm 1440 coupled to each other by a beamsplitter 1420. As further illustrated in FIG. 14, the beamsplitter 1420 is also coupled to a frequency sampled detection module 1431 over a detection path 1406 that may be provided by an optical fiber.

As further illustrated in FIG. 14, the source 1400 is coupled to the beamsplitter 1420 by a source path 1405. The source 1400 may be, for example, a broadband comb source. The reference arm 1410 is coupled to the beamsplitter 1420 over a reference arm path 1407. Similarly, the sample arm 1440 is coupled to the beamsplitter 1420 over the sample arm path 1408. The source path 1405, the reference arm path 1407 and the sample arm path 1408 may all be provided by optical fiber.

In some embodiments, the reference arm 1410 may be a phase modulated reference arm or a frequency-shifted reference arm as illustrated in FIG. 14, although embodiments of the present invention are not limited to this configuration. Furthermore, the sample arm 1440 may include scanning delivery optics and variable optics 1460. Also illustrated in FIG. 14 is the reference plane 1450 and a representation of a depth doubled imaging window 1470 in accordance with some embodiments of the present inventive concept.

Figure 16:
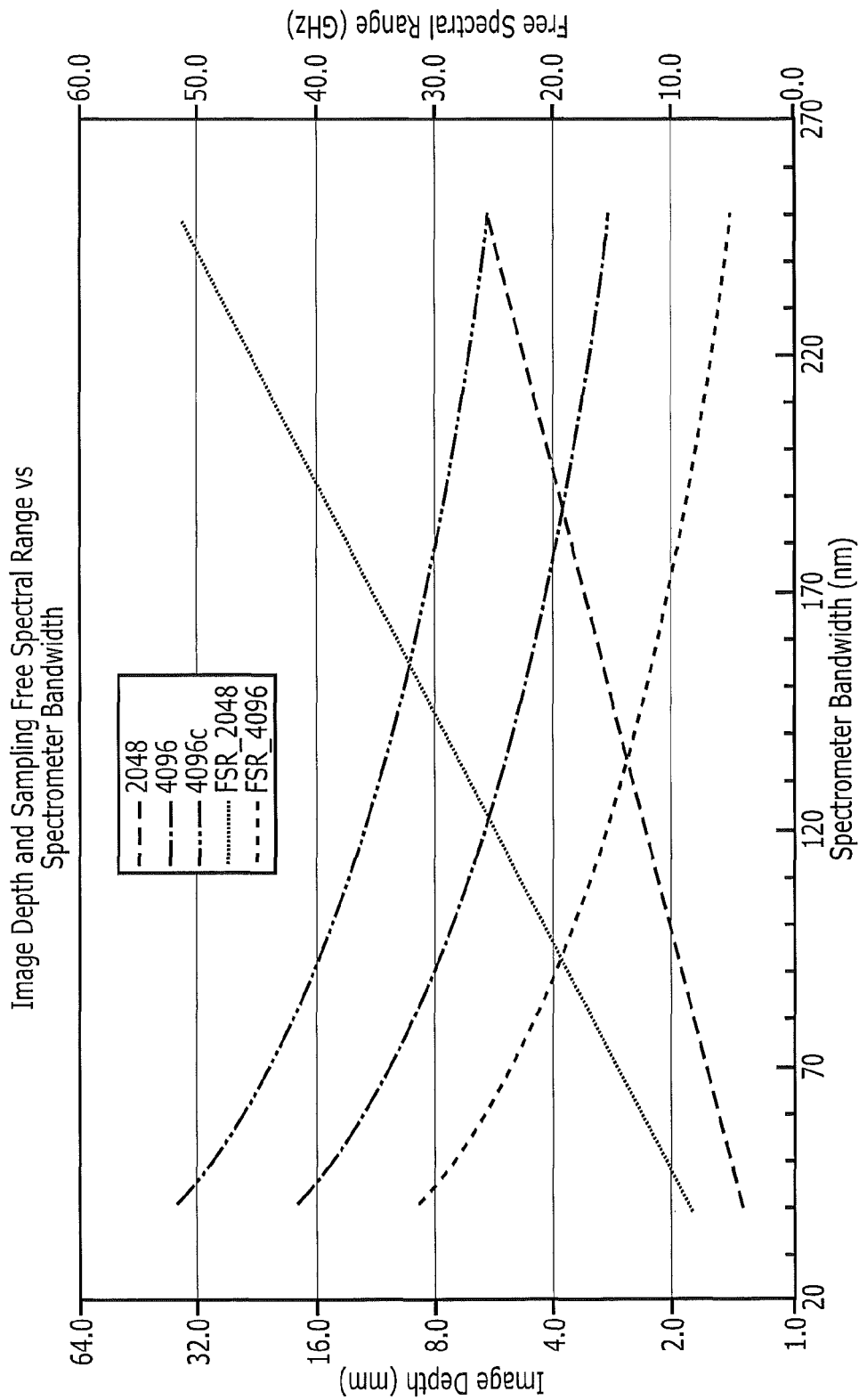
FIG. 16 is a graph illustrating image depth and sampling free spectral range vs. spectrometer bandwidth for an extended depth FDOCT system in accordance with some embodiments of the present inventive concept.

FIG. 15 is a graph illustrating depth and resolution vs. spectrometer bandwidth and samples for an extended depth FDOCT system in accordance with some embodiments discussed herein. FIG. 16 is a graph illustrating image depth and sampling free spectral range vs. spectrometer bandwidth for an extended depth FDOCT system in accordance with some embodiments of the present inventive concept. FIG. 15 illustrates the relationship between resolution and total imaging bandwidth, given single sided imaging at 2048 samples and 4096 samples, and complex conjugate resolved imaging at 4096 samples. As the bandwidth is constrained to increase image depth, resolution suffers. FIG. 16 illustrates the same bandwidth and sampling dependence of image depth, as well as the effective free spectral range associated with k-linearized sampling.

Embodiments of the present invention directed to spectral domain OCT (SDOCT) will now be discussed. It will be understood that both SDOCT and SSOCT implementations will be discussed in detail herein. The selection of SDOCT or SSOCT is a function of desired imaging wavelength, availability of sources, and tradeoffs between key attributes, such as imaging speed and resolution. Implementations have been shown in the art that combine elements of SDOCT and SSOCT, and such implementations may benefit from application of the present inventive concept.

Referring again to FIG. 14, an SDOCT system in accordance with embodiments discussed herein includes a broadband optical source 1400, a source path 1405, a beam splitter/combiner 1420, a reference path 1407, a reference reflector 1410, a sample path 1408 with a scanning system and focal optics 1440/1460 configured to appropriately to image structures of the sample, such as the cornea, anterior chamber, iris, lens, posterior chamber, and retina of the eye, a detector path 1407, and a spectrographic detection system 1431.

In some embodiments, the SDOCT system is designed to image structures of the eye in the 800 nm to 900 nm wavelength range. The system may be designed to have a single-sided imaging depth (as measured in air) of about 7.0 mm, suitable for imaging the crystalline lens of the eye, and a complex-conjugate resolved imaging depth of about 14.0 mm, suitable for full range imaging of anterior of the eye, from corneal apex through the crystalline lens. Through translation of the reference arm 1407 and change in scanning and focal attributes of sample arm optics, the system is capable of imaging the entire optical structure of the eye in three steps.

In some embodiments, the broadband optical source 1400 is a superluminescent diode with a bandwidth of between about 40 nm and about 80 nm. The bandwidth of the source may be selected for axial resolution, but the useful bandwidth may be constrained by the total bandwidth of the detector. In some embodiments, the spectral characteristics of the source are such that the spectral power density at the edges of the spectrometer are attenuated at least about 6 dB from the peak power density, and may be about 10 dB. If the optical power at the edges of the spectrometer is too high, the image may exhibit ringing around bright features; numerical windowing of the acquired spectrum will reduce this artifact. The parameters of the numerical windowing may be selected to reduce the ringing by smoothly attenuating the signal to meet the stated conditions. For example, a cosine-squared window may be applied to the data immediately prior to the Fourier transform, or a raised Gaussian function may be applied ($e^{x-4}$).

Although embodiments are discussed herein as having a superluminescent diode for the broadband optical source 1440, embodiments of the present invention are not limited to this configuration. However, the superluminescent diode may be the most cost effective in this application, where ultra-wide bandwidth may not be required.

In some embodiments, the paths may be combined using single-mode optical fiber, such as Corning HI780. A fiber optic coupler may be used as the beam splitter/combiner 1420. The splitting ratio of the coupler can be chosen to optimize power to the sample and signal-to-noise ratio of the detection system. In some embodiments, the splitter 1420 may have a 80/20 split ratio, with 20% of the source light directed to the sample and 80% directed to the reference arm.

The reference path directs light from the coupler to an optical reflector. The path length of the reference arm may be designed to match the path length to the region of interest for the sample under test. In some embodiments, the reference arm 1407 has a translation capability to adjust to varying regions for a sample under test, which may be particularly important for imaging at multiple depths within one sample, such as an eye. The reference arm 1407 may be continuously translated, translated in steps through switches to predetermined path lengths, or a combination of the two without departing from the scope of the present inventive concept. Generally, the reference arm may be finely adjustable to a precision of at least about 100 µm to accurately position the sample within the FDOCT imaging window 1470.

The sample arm 1408 includes scanning optics, preferably scanners configured to scan a beam to any position within a field of view; scanning may be continuous, as with galvonometric scanners, or discontinuous, using, for example projecting a beam onto a spinning diffractive structure without departing from the scope of embodiments discussed herein. The optics used to deliver the scanned beam to the subject are discussed in, for example, U.S. Patent Publication No. 2008/0106696 incorporated by reference above, for imaging of the anterior structures of the eye, nominally telecentric scanning focused onto anterior structures, or scanning design to pivot in the pupil of the eye for scanning an imaging of posterior structures.

The spectrographic system images the output of the dispersed interference signal onto a CCD (Atmel, DALSA) or CMOS (Basler) array, as is well known in the art. For extended depth imaging with 7 mm single-sided imaging depth, a source with central wavelength of 840 n and a FWHM bandwidth of 65 nm imaged onto a 4096 element array with 14 micrometer pixel width may be used. As outlined in the Table of FIG. 17, the edged-to-edge bandwidth of the array is 103 nm, and the source decays to 6 dB of peak power at the edge of the array. The frequency spacing of central pixels is 10.7 GHz. In a traditional spectrometer that utilizes a volume phase holograph transmission grating, there may be significant frequency chirp from the blue edge to the red edge, leading to the need for resampling discussed earlier.

Figure 18A:
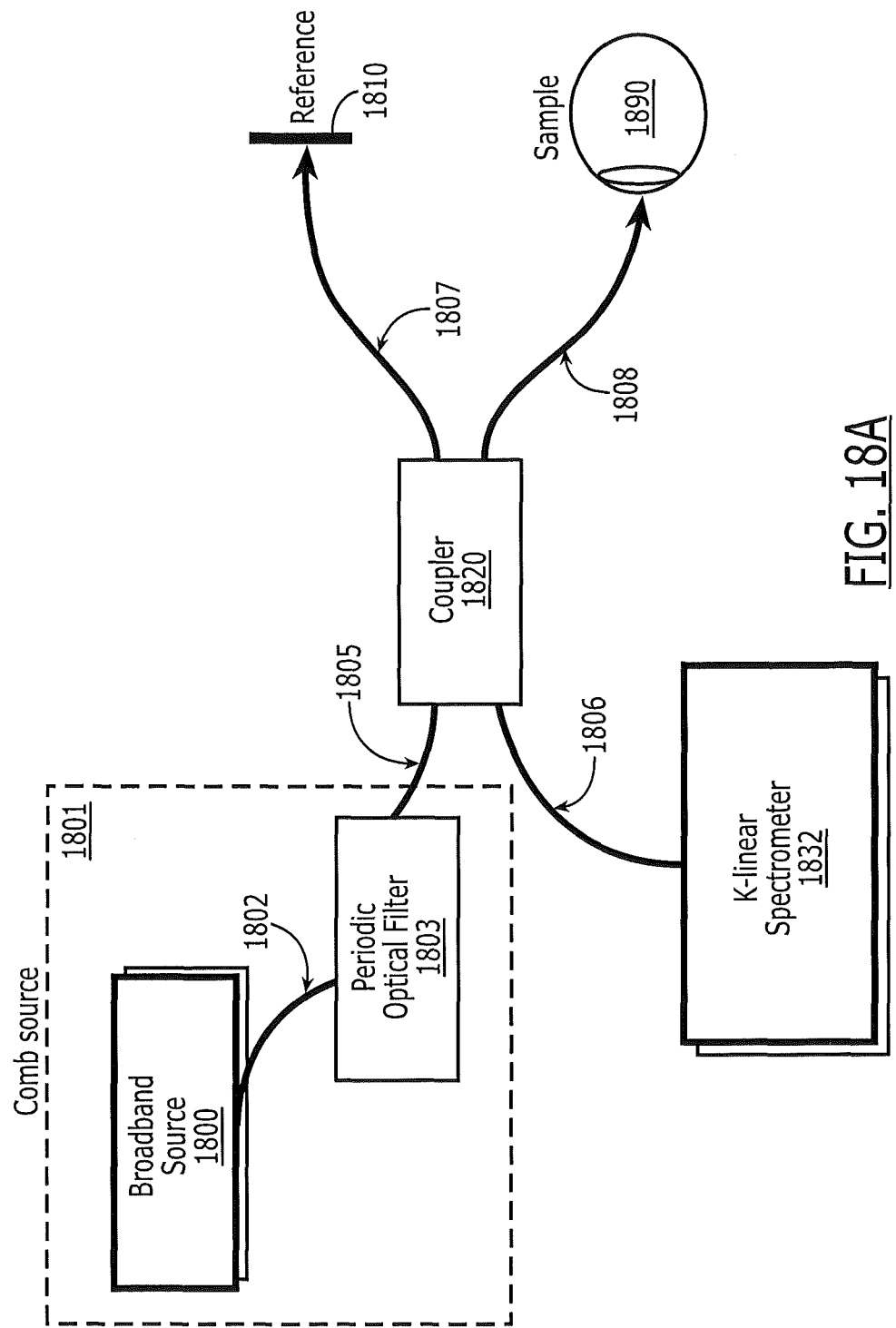
FIGS. 18A through 18C are block diagrams illustrating various embodiments of extended-depth FDOCT imaging systems in accordance with some embodiments of the inventive concept.
Figure 18B:
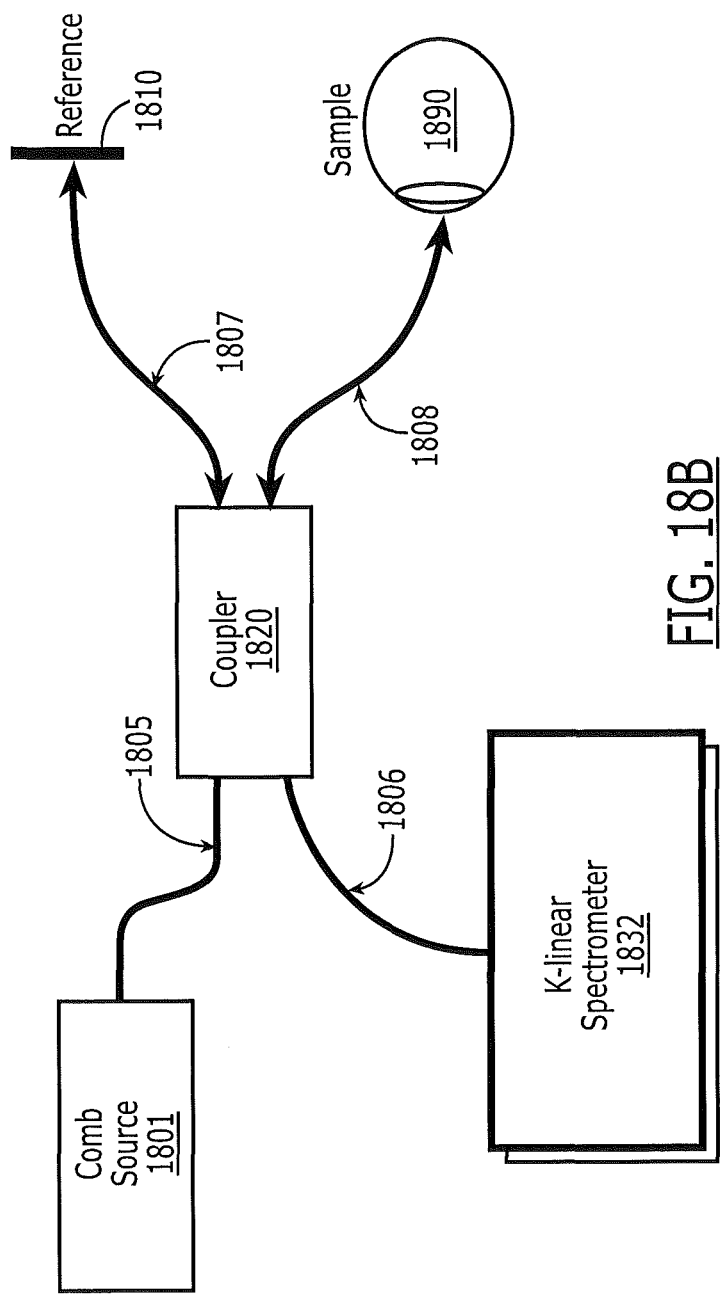
Figure 18C:
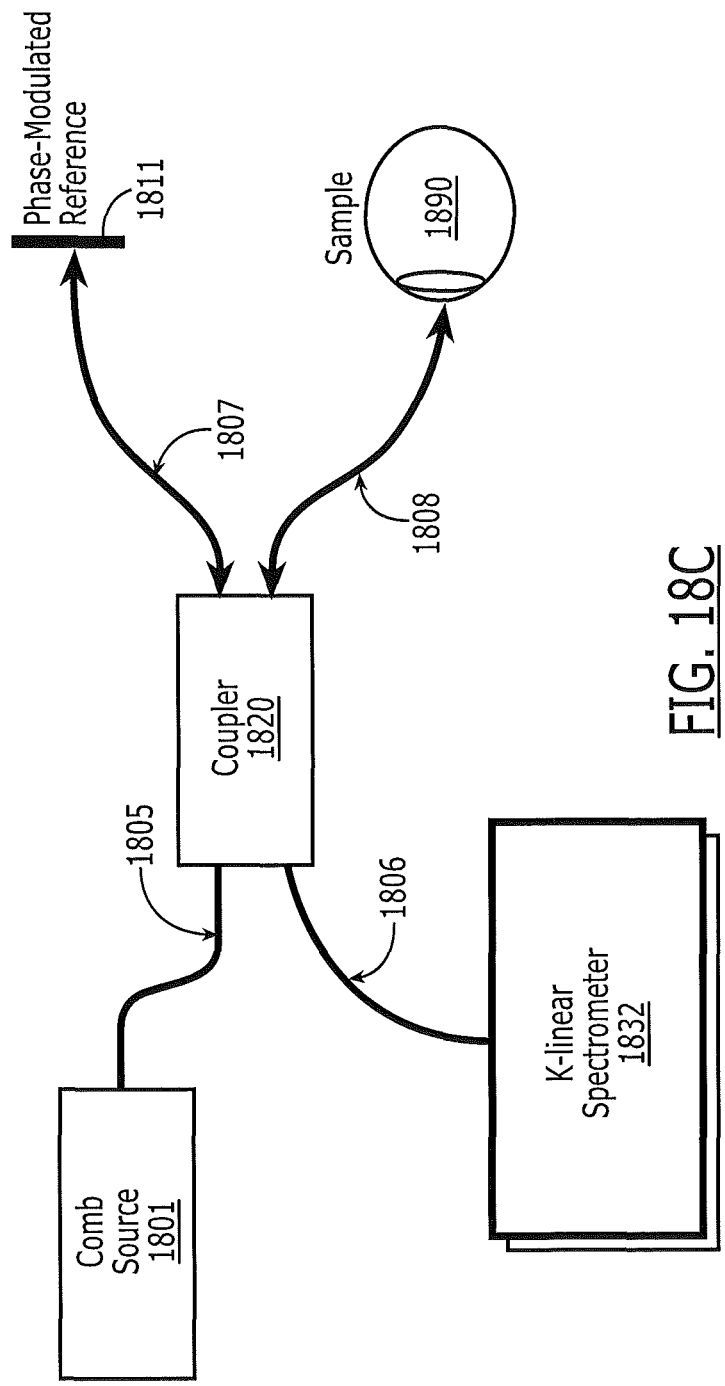

In some embodiments of the present inventive concept, the spectrometer will be of a constant-dispersion, or k-linearized type as illustrated in FIGS. 18A through 18C, k-linear spectrometer 1832. It will be understood that this may be performed by replacing the VPH grating with a GRISM—a grating-prism pair discussed above with respect to FIGS. 7-10—or a chirped grating replicating a GRISM as discussed above. In some embodiments, the prism is a high index glass (Schott P-SF68, n=2.0), with a vertex angle of $\pi/8$ radians (FIG. 7). The prism is in optical contact with the grating. The grating is a low-spatial frequency grating (400 lines/mm), sandwiched between faces of Schott B-270 (n=1.52). The prism angle of incidence α is 22.5 degrees. A high index prism is typically necessary in order that the total internal reflection condition of the grating is reduced or possibly avoided. An air-spaced prism-grating combination may be used to provide additional design functionality, but is not necessary in all cases. The collimated beam input to the prism may be 25 mm in diameter. The dispersed output from the grating couples to a 220 mm focal system, yielding a <10 micrometer spot size on the pixels across the array. The Nth frequency channel maps to the Nth pixel to within 50% of the pixel width across the array.

In some embodiments, the spectrum may be channelized to the spectrometer using the periodic optical filter 1803 illustrated in FIG. 18A. In some embodiments, the filter 1803 may be a fabry-Perot etalon (discussed above) illustrated in FIG. 20, which will be discussed further below. In some embodiments, the filter 1803 may be an AR coated glass block of index 1.55 with FSR of 10.7 GHz and Finesse of two. Operating at angle of $\pi/8$ degrees to normal to avoid backreflections into the diode, the thickness of the block is 9.79 mm. To achieve a finesse of 2, the reflectivity of the AR coatings must be 41%. For a finesse of 8, reflectivity is 92.7%, further improving sensitivity falloff, but at the cost of required source power. As the linearity of the spectrometer will be calibrated, precision of the central frequency of the etalon as a reference point is not a primary concern. Athermalization may be required not so much to control shifts in the channelized spectrum, but to control changes to FSR. Athermalization techniques are known in the art; the degree of athermalization required is to keep the FSR constant to within 25%. An alternative to an athermalized glass block is to use a piezo controlled cavity; the cavity spacing would increase to 15.2 mm for an air index n=1.

The combination of the k-linear spectrometer and the filtered source bandwidth yields a (single-sided) deep imaging SDOCT system with superior sensitivity falloff characteristics. The addition of phase modulation to the reference arm as discussed in U.S. Pat. No. 7,742,174 or U.S. Patent Publication No. 2008/0002183. In some embodiments, a piezo-driven retroreflector 1811 as illustrated in FIG. 18C modulates the phase of the reference arm from its nominal position. In principle, the phase of the reference arm can be modulated in steps of $\Pi/4$ for acquisition multiple phase-stepped acquisitions at a specific A-scan location.

In practice, to continuously modulate the scan; the phase information can be determined by integrating over the $\pi/4$ steps using an integrating buckets approach. Note that it may not be necessary for the phase steps to be $\pi/4$; $\pi/3$, for example, works as well. The optimal number of steps is a function of the level of isolation between the real and the mirror image, and the phase stability of the subject. To the latter point, rapid image acquisition may be preferred. In some embodiments, a CMOS or CCD camera with acquisition speeds of at least 70 kHz are desired. In a four phase-step acquisition, a single A-scan is acquired at 17 kHz, which is suitably fast for real-time display of full range cross sectional images. As cameras are now available at 140 kHz, a target full range line rate of 34 kHz (1000 line frame rate of 34 Hz) is practical.

Note as well that it may not be necessary that that the scanning mirrors remain fixed at a specific A-scan location. Phase modulation and acquisition of sequential A-scans is acceptable so long as the A-scans are optically oversampled at a similar ratio as implied in the per-A-scan acquisition scenario. Thus sinusoidally scanning over $\pi$ radians at each A-scan and acquiring four samples is functionally equivalent to linearly modulating at a rate of $\pi$ radians over four sequential 4× oversampled A-scans.

If the amplitude, phase and frequency of the modulation are set as specified in U.S. Pat. No. 7,742,174, then the resulting A-scan should theoretically be completely free of DC, autocorrelation, and complex conjugate artifacts. However, slight deviations from perfection in achieving these parameters may be experienced in any real physical implementation of sinusoidal phase modulation and may lead to a degradation of performance compared to the ideal result in the form of incomplete complex conjugate artifact suppression. Thus, an additional step of applying quadrature projection processing according to FIG. 2 of U.S. Patent Application Publication No. 2008/0170219 may be applied to improve the complex conjugate artifact rejection, at the cost of a small amount of reduced signal to noise ratio. Quadrature projection processing is an algorithmic step which does not require any hardware modification and which reduces the complex conjugate artifact from imperfectly phase modulated SDOCT data by forcing the real and imaginary parts of the recorded A-scan signal to be orthogonal.

Figure 25:
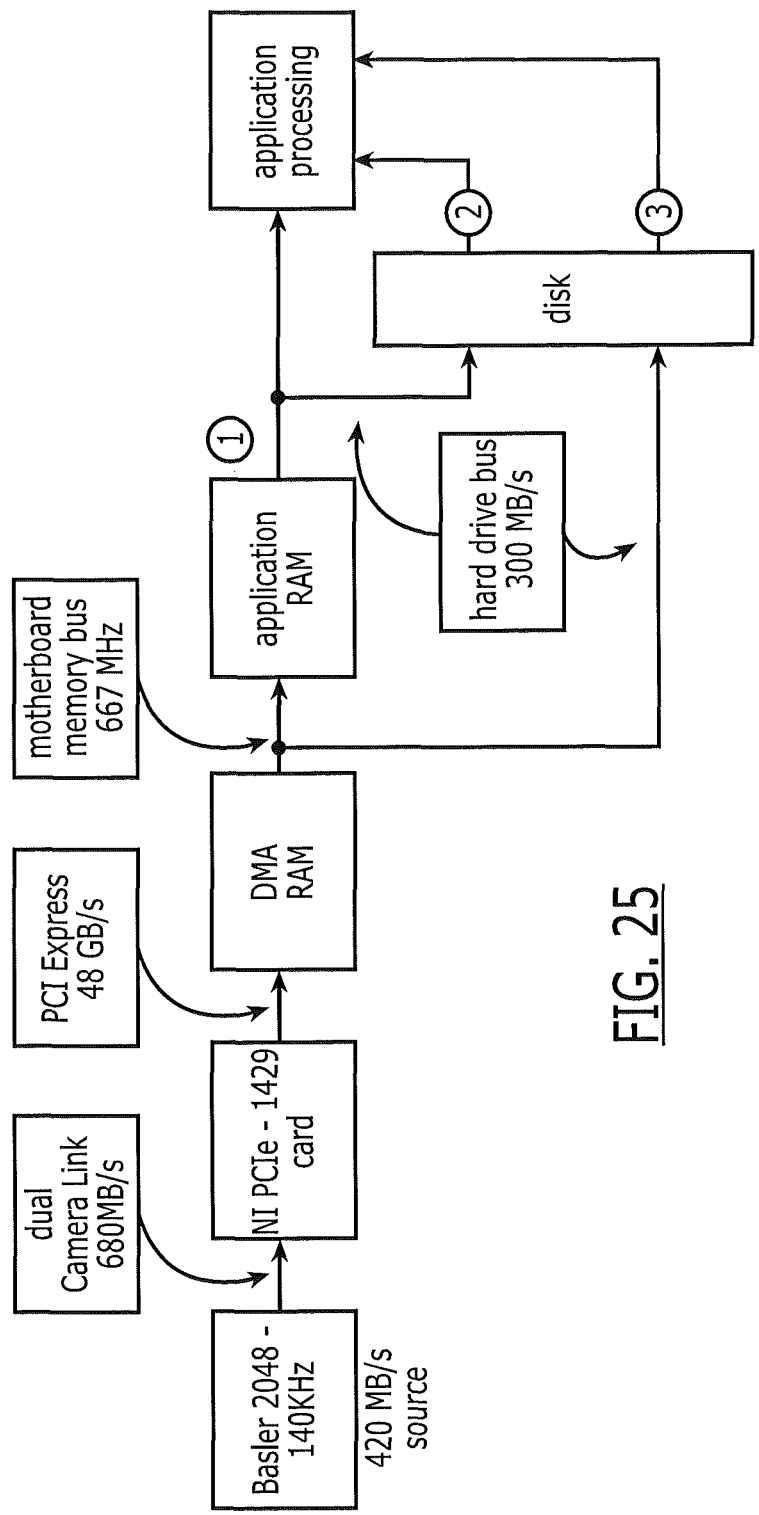
FIG. 25 is a block diagram illustrating data flow of an SDOCT system in accordance with some embodiments.
Figure 26:
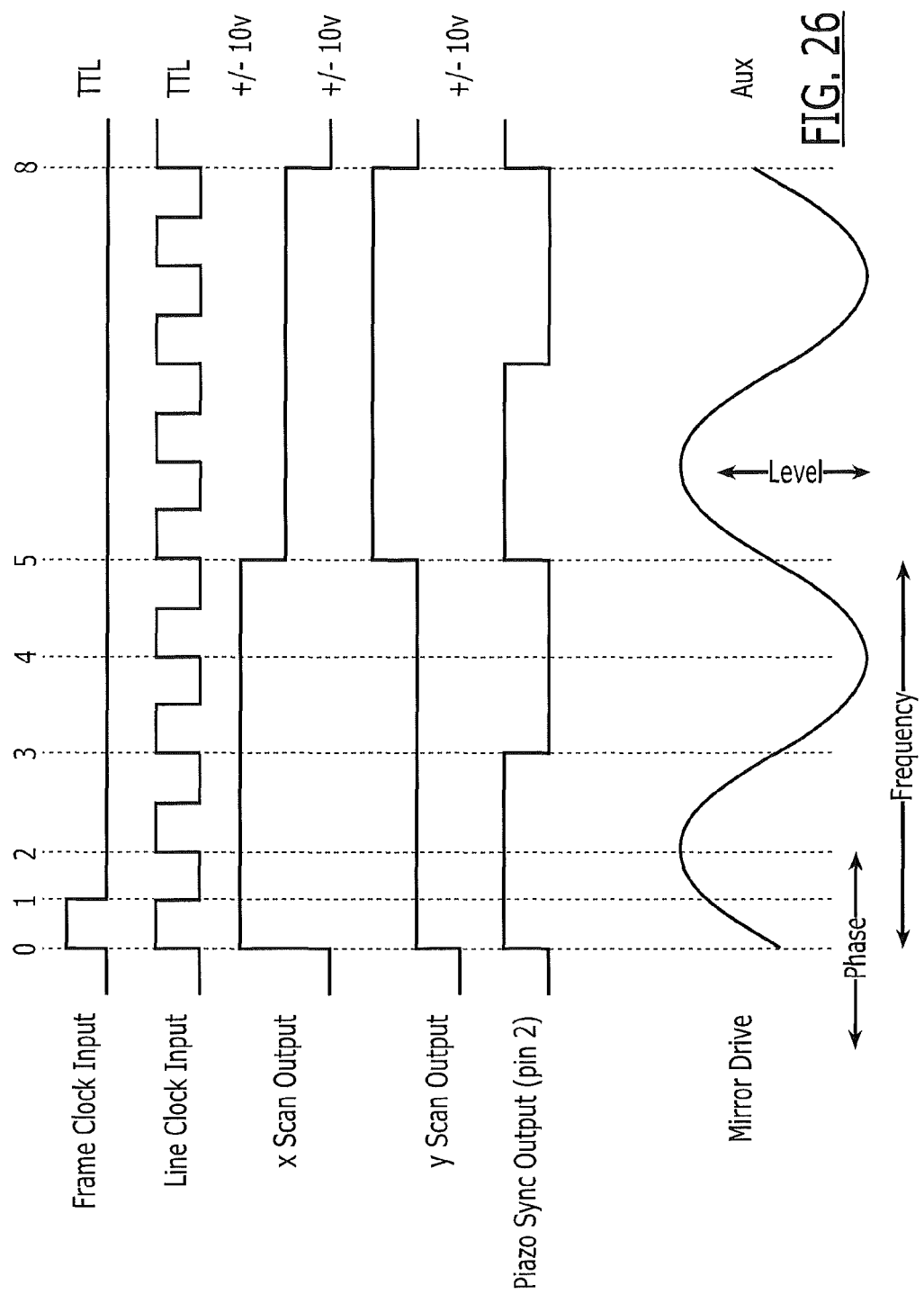
FIG. 26 is a complex conjugate removal (CCR) control timing diagram in accordance with some embodiments.

FIG. 25 is a block diagram illustrating data flow in some embodiments of SDOCT imaging systems in accordance with embodiments discussed herein. As illustrated, the prime bottleneck to stream-to-disk acquisition is not the PCI Bus or motherboard memory bus but the hard drive bus, which is typically limited to 300 MB/s per bus for a SATA drive. FIG. 26 illustrates a CCR control timing diagram. As illustrated therein, every fourth line clock is phase locked to the mirror drive and as such the piezo sync output is locked to the line output.

Figure 19:
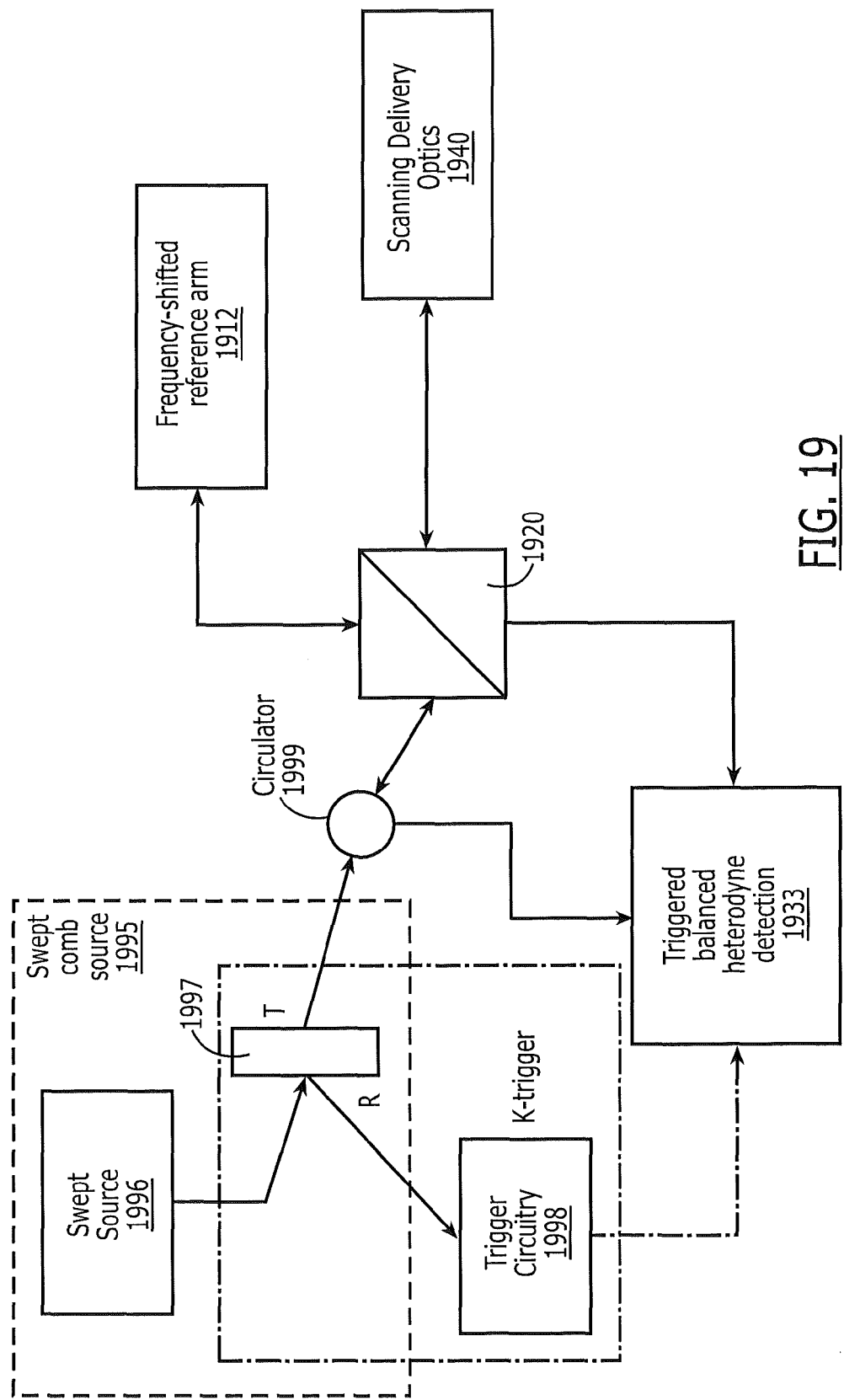
FIG. 19 is a block diagram of an FDOCT system including a swept source and optical filter in accordance with some embodiments.

Referring now to FIG. 19, an SSOCT system designed for comprehensive ocular imaging according to some embodiments of the present invention will be discussed. In some embodiments, complex conjugate removal (CCR) is the so-called "heterodyne" CCR method, which involves introducing a frequency shift between the sample and reference arm light and thus shifting the carrier frequency of the image-bearing signal away from DC, about which the complex conjugate artifact is centered as discussed in U.S. Pat. No. 7,336,366. With the addition of this frequency shift, the A-scan free of complex conjugate artifact is found from the Fourier transform of the detected signal, centered at the frequency shift value. If an A/D converter is used which has much higher bandwidth than the SSOCT signal itself, then the frequency shift value can be set to be many times the frequency encoding the $z_{max}$ value of the A-scan, thus the complex conjugate artifact will be located far in frequency space away from the A-scan data. If a very high sweep speed is employed, however, such that the SSOCT signal already occupies a substantial fraction of the A/D converter bandwidth, then the complex conjugate artifact may only be shifted to the borders of the depth-doubled A-scan. This method of heterodyne CCR is consistent and will not interfere with the embodiments described above for switching between sample and reference arm imaging modes, switching SSOCT imaging depth, and switching of the comb filter FSR spacing to remain consistent with the spectral sampling interval.

As illustrated in FIG. 19, the SSOCT system includes a swept comb source 1995, a circulator 1999, a beamsplitter 1920, a triggered balanced heterodyne detector 1933, a frequency-shifted reference arm 1912 and scanning delivery optics 1940 in the sample arm. As further illustrated in FIG. 19, a fabry-Perot etalon (discussed above) 1997 and a swept source 1996 can be used to provide a swept comb source. A practical etalon may be composed of a glass block with 2 partially reflecting surfaces. As discussed above, the two key attributes of the etalon are the free spectral range (FSR) and the Finesse. The FSR determines the sampling interval, which in some embodiments is designed to match the desired sampling interval, for example, the pixel spacing of the k-linear spectrometer or the k-trigger 1998 of the light source. The FSR is closely related to the optical path length through the etalon, which may be angle tuned according to equation 34. The Finesse sets the spectral width at each output frequency, or the duty cycle of the etalon transmission function. The Finesse is closely related to the reflectivity of the interfaces of the etalon. As further illustrated in FIG. 19, it is further advisable to use an optical isolator or circulator 1999 after the filter and before coupler 1920, as signal returned from sample and reference arm will experience a complementary interaction with etalon, and multi-path interference may degrade image quality.

Figure 20:
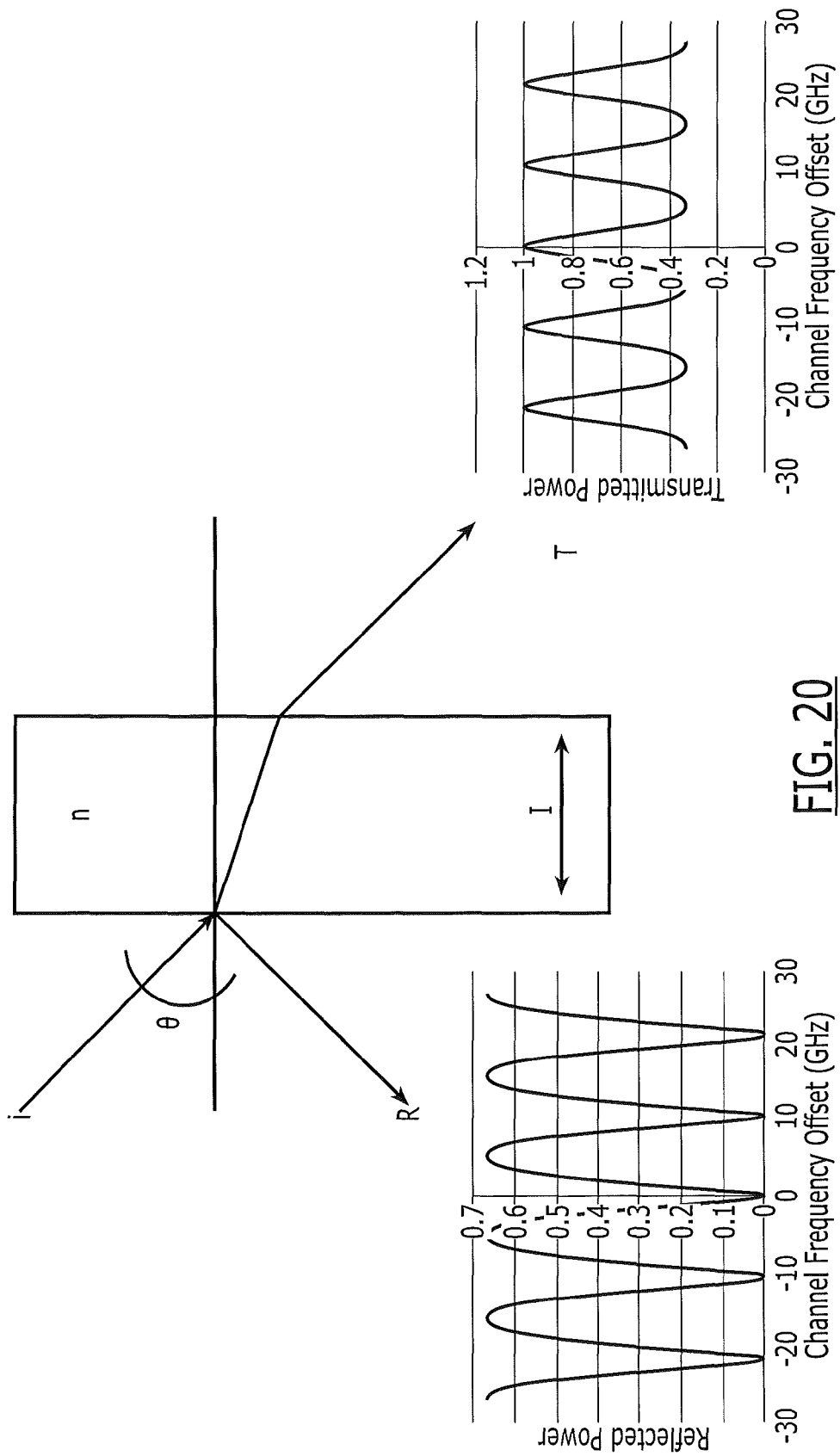
FIG. 20 is a block diagram illustrating an optical filter configuration in accordance with some embodiments.
Figure 21:
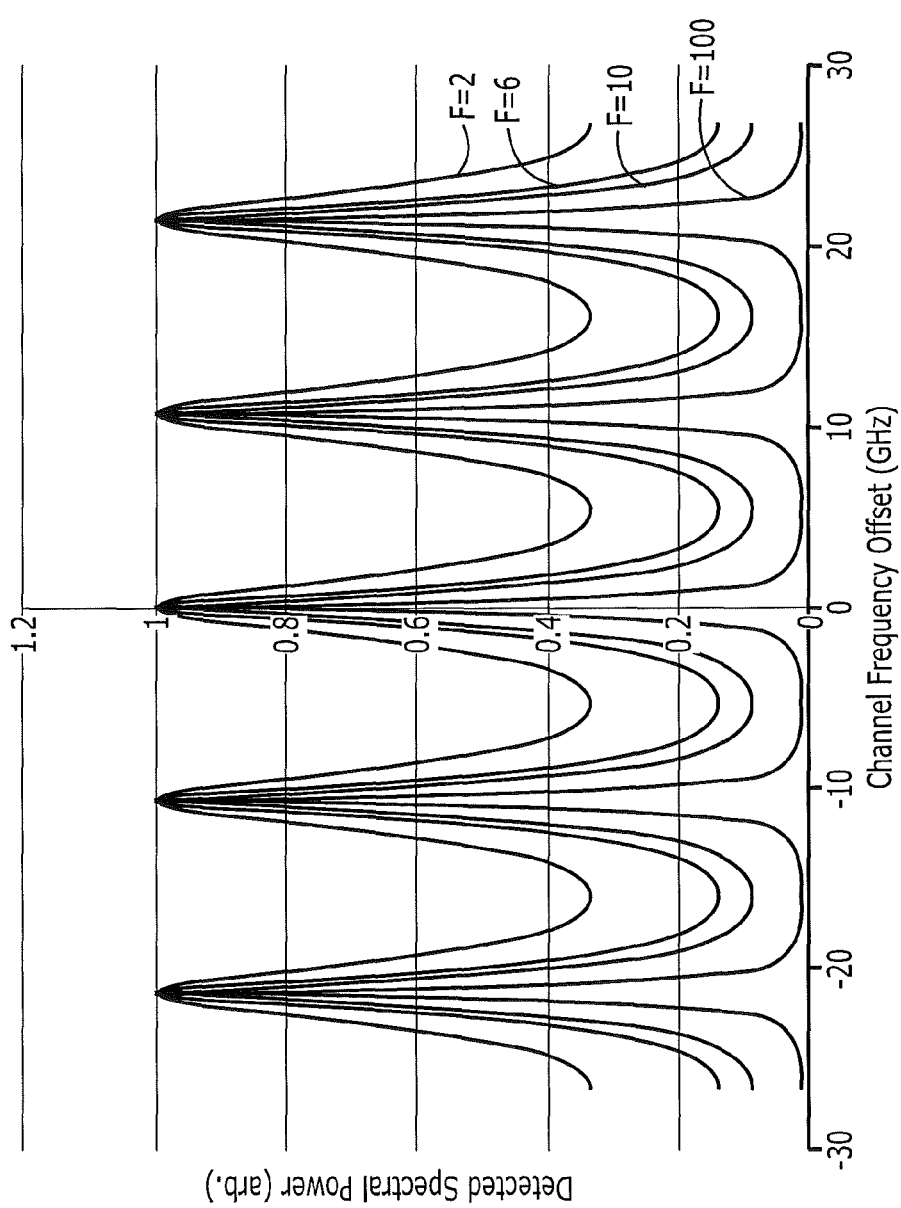
FIGS. 21 through 24 are graphs illustrating various aspects of output of the optical filter of FIG. 20 in accordance with some embodiments.
Figure 22:
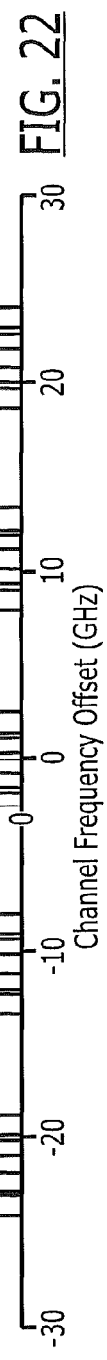

FIG. 20 is a detailed block diagram of the periodic filter 1997 of FIG. 19. Also illustrated in FIG. 20 are graphs of reflected (R) and transmitted (T) power that is output from the filter. FIG. 21 further illustrates a graph depicting the output of the periodic filter of FIG. 20. FIG. 22 is a graph illustrating an effective duty cycle of the periodic optical filter of FIG. 20. FIG. 23 is a graph illustrating SNR falloff as a function of pixel fill factor (duty cycle). As illustrated therein, as the fill factor decreases from 100% down to 50% (Finesse=2), for the 7 mm single-side imaging system discussed herein, the 3 dB falloff depth increases from about 1.34 mm to nearly 2.68 mm. Decreasing further to a 15% fill factor pushes the 3 dB depth beyond the maximum depth. Coupled with CCR, this technique could increase the total imaging range with SNR loss to a full 14 mm range with 1.8 dB SNR loss at the edges for Finesse=6. Finally, FIG. 24 is a graph comparing reflected and transmitted power of the optical filter of FIG. 20.

Some embodiments for a comprehensive ocular imaging system using swept source (SSOCT) design have a zmax=7 µm, thus the imaging depth capability of this system after complex conjugate removal is 14 mm optical path length. As illustrated in FIG. 19, for a swept source implementation, the light source may be a swept source laser 1996 having a center wavelength near 1060 nm, an instantaneous coherence length (before filtering) of 5 mm, and a full-scanning optical bandwidth of approximately 100 nm. Light from the laser is directed into a 50:50 single mode coupler 1920 and then into sample and reference arms.

As in the SDOCT implementation, the reference path directs light from the coupler to an optical reflector 1912 that is designed to match the path length to the region of interest for the sample under test. Positioning capabilities of the SSOCT reference arm are the same as for the SDOCT reference arm. However, in some embodiments, rather than the phase modulator of the SDOCT configuration, the SSOCT configuration possesses an acousto-optic modulator (AOM) operating at 250 MHz acoustic frequency for heterodyne complex conjugate artifact removal. The sample arm may also possess an AOM operating at 250 MHZ plus a differential frequency, as discussed in U.S. Pat. No. 7,336,366.

Light returning from the sample and reference arms is recombined in the 2×2 coupler and detected by a 500 MHz bandwidth optical photoreceiver. A/D conversion is performed with 12 bit resolution at 500 MHz sampling rate in order to obtain $2*z_{max}$=14 mm optical path length.

Previously demonstrated implementations of heterodyne complex-conjugate removal in SSOCT systems utilized a pair of phase modulators (either acousto-optic or electro-optic) arranged to give a net difference phase modulation frequency on the order of hundreds of kHz to tens of MHz. This was done with either one modulator placed in each of the reference and sample arms, or two modulators arranged in series in a single arm. With source sweep frequencies of less than about 20 kHz, this arrangement gives a sufficiently high heterodyne modulation frequency to allow for good separation of the complex-resolved A-scan signal away from DC. With an increased sweep rate of approximately 100 kHz, a single acousto-optic or electro-optic modulator operating at approximately 350-500 MHz modulation frequency may be placed in the reference arm, as illustrated in FIG. 19. If the photoreceiver and A/D conversion circuitry have a bandwidth of 700-1000 MHz, then the frequency modulation will place the zero path length position of the A-scan near the middle of the detection bandwidth, thus effectively resolving the complex conjugate artifact for these rapid scan rates.

The same periodic filter structure described for the SDOCT system is applied to the SSOCT to increase the instantaneous coherence length of the source (by reducing the sampled linewidth). A variable length piezo-driven etalon may be used in order that the frequency spacing of the output peaks may be changed to change the single-sided depth of the image. At 10.71 GHz, a 7 mm single-sided window imaging window may be achieved. The number of samples acquired determines the wavelength range utilized, and thus enables a tradeoff between resolution and acquisition speed. At 2048 samples, the sampled wavelength range will be 82 nm, and the resolution will be approximately 10 micrometers. The reflective port of the periodic filter acts directly as the k-trigger for sampling the interference signature. As the etalon FSR is modified, for example from 10.7 GHz to 5.35 GHz, the single-sided imaging depth is increased from 7 mm to 14 mm. The k-trigger automatically tracks. This capability to change imaging depth is an important attribute of this SSOCT architecture, allowing an imaging system to rapidly change depth of imaging field as the situation requires.

For SDOCT, one can imagine a hardware switchable spectrometer wherein the sampling interval is modified. A simple approach to reduce image depth is to process every second pixel on an array. In some embodiments, a spectrometer can be constructed to double the imaging depth.

In the drawings and specification, there have been disclosed exemplary embodiments of the invention. However, many variations and modifications can be made to these embodiments without substantially departing from the principles of the present invention. Accordingly, although specific terms are used, they are used in a generic and descriptive sense only and not for purposes of limitation, the scope of the invention being defined by the following claims.

That which is claimed is:

1. An extended depth Fourier Domain Optical Coherence Tomography (FDOCT) imaging system, the system comprising:
    an optical source having a bandwidth;
    an optical detection system having a first mode of operation configured to sample a first plurality of spectral elements within the bandwidth of the optical source at substantially equal optical frequency intervals, wherein the optical frequency interval is less than or equal to about 10.7 GHz and wherein a number of sampled elements is greater than or equal to 1024; and
    a reference arm, a sample arm and an optical combiner, the optical combiner being configured to couple the reference arm and the sample arm to the optical detection system,
    wherein a transform is applied to a set of the sampled first plurality of spectral elements to derive spatial domain data; and
    wherein a reference arm path length associated with the reference arm and a sample arm path length associated with the sample arm are configured to set a position of an image of a structure of a sample within a spatial domain image window.

2. The system of claim 1:
wherein the optical detection system further has a second mode of operation configured to sample a second plurality of spectral elements within the bandwidth of the optical source;
wherein a transform is applied to a set of the sampled second plurality of spectral elements to derive spatial domain data; and
wherein the optical frequency interval of the set of the sampled second plurality of spectral elements in the second mode of operation is no less than two times wider than the optical frequency interval of the set of the sampled first plurality of spectral elements in the first mode of operation.

3. The system of claim 1:
wherein the optical detection system has a second mode of operation configured to sample a second plurality of spectral elements within the bandwidth of the optical source;
wherein a transform is applied to a set of the sampled second plurality of spectral elements to derive spatial domain data; and
wherein a number of spectral elements in the set of the sampled second plurality of spectral elements applied in the second mode of operation is no greater than one half a number of spectral elements in the set of the sampled first plurality of spectral elements applied in the first mode of operation.

4. An extended depth Fourier Domain Optical Coherence Tomography (FDOCT) imaging system, the system comprising:
an optical source having a bandwidth;
an optical detection system having a first mode of operation configured to sample a first plurality of spectral elements within the bandwidth of the optical source at substantially equal optical frequency intervals, wherein the optical frequency interval is less than or equal to about 10.7 GHz and wherein a number of sampled plurality of element greater than or equal to 1024; and
an adjustable reference arm, a sample arm and an optical combiner, the optical combiner configured to couple the reference arm and the sample arm to the optical detection system,
wherein a transform is applied to a set of the sampled first plurality of spectral elements to derive spatial domain data; and
wherein a reference arm path length associated with the reference arm and a sample arm path length associated with the sample arm are configured to set a position of an image of a first structure of a sample within the spatial domain image window.

5. The system of claim 4:
wherein the optical detection system has a second mode of operation configured to sample a second plurality of spectral elements within the bandwidth of the optical source;
wherein a transform is applied to a set of the sampled second plurality of spectral elements to derive spatial domain data; and
wherein the optical frequency interval of the set of sampled second plurality of spectral elements in the second mode of operation is no less than two times wider than the optical frequency interval of the set of sampled first plurality of spectral elements in the first mode of operation.

6. The system of claim 4:
wherein the optical detection system has a second mode of operation configured to sample a second plurality of spectral elements within the bandwidth of the optical source;
wherein a transform is applied to a set of the sampled second plurality of spectral elements to derive spatial domain data; and
wherein the number of elements in the set of sampled second plurality of spectral elements applied in the second mode of operation is no greater than one half the number of elements in the set of sampled first plurality of spectral elements applied in the first mode of operation.

7. The system of claim 4, further comprising:
a second reference arm path length associated with the reference arm configured to set a position of an image of a second structure of a sample within the spatial domain image window.

8. An extended depth Fourier Domain Optical Coherence Tomography (FDOCT) imaging system, the system comprising:
an optical source having a bandwidth;
an optical detection system having a first mode of operation configured to sample a first plurality of spectral elements within the bandwidth of the optical source, wherein the optical frequency interval between adjacent sampled first plurality of spectral elements is no greater than 10.7 GHz and wherein a number of sampled plurality of elements is no less than 1024; and
a reference arm, a sample arm and an optical combiner, the optical combiner being configured to couple the reference arm and the sample arm to the optical detection system,
wherein a transform is applied to a set of the sampled first plurality of spectral elements to derive spatial domain data; and
wherein a first reference arm path length associated with the reference arm and a first sample arm path length associated with the sample arm are configured to set a position of an image of a first structure of a sample within the spatial domain image window.

9. The system of claim 8:
wherein the optical detection system has a second mode of operation configured to sample a second plurality of spectral elements within the bandwidth of the optical source;
wherein a transform is applied to a set of the sampled second plurality of spectral elements to derive spatial domain data; and
wherein the number of elements in the set of the sampled second plurality of spectral elements applied in the second mode of operation is no greater than one half the number of elements in the set of the sampled first plurality of spectral elements applied in the first mode of operation.

10. The system of claim 8:
wherein the optical detection system has a second mode of operation configured to sample a second plurality of spectral elements within the bandwidth of the optical source;
wherein a transform is applied to a set of the sampled second plurality of spectral elements to derive spatial domain data; and
wherein the optical frequency interval of the set of sampled second plurality of spectral elements in the second mode of operation is no less than two times wider than the optical frequency interval of the set of sampled first plurality of spectral elements in the first mode of operation.

11. The system of claim 8, further comprising a second reference arm path length associated with the reference arm configured to set a position of an image of a second structure of a sample with the spatial domain image window.

12. The system of claim 8:
wherein the sample is an eye; and
wherein the first structure of the sample comprises one or more of a surface of a cornea, a cornea, an anterior segment, an iris, a surface of a lens, a lens, a posterior segment, a surface of a retina and a retina.

13. The system of claim 8, wherein the optical source is a broadband source having a wavelength in the range of from about 800 nm to about 1200 nm.

14. The system of claim 8, wherein the optical source is a swept source having a wavelength in the range of from about 800 nm to about 1200 nm.

15. The system of claim 8, wherein the optical source is a comb source having a wavelength in the range of from about 800 nm to about 1200 nm.

16. The system of claim 11:
wherein the second reference arm path length differs from the first reference arm path length by a distance no less than twice a depth of the spatial domain imaging window.

17. The system of claim 11:
wherein the second reference arm path length differs from the first reference arm path length by a distance no less than one-half a combined length of first and second structures of the sample to be imaged.

18. The system of claim 8, wherein the optical detection comprises a wavenumber-linear spectrometer.

19. An extended depth Fourier Domain Optical Coherence Tomography (FDOCT) imaging system, the system comprising:
an optical source having a bandwidth;
an optical detection system configured to sample a plurality of spectral elements within the bandwidth of the optical source; and
a reference arm, a sample arm and an optical combiner, the optical combiner being configured to couple the reference arm and the sample arm to the optical detection system,
wherein a transform is applied to a set of the sampled plurality of spectral elements to derive spatial domain data;
wherein the imaging system comprises a first mode of operation and a second mode of operation;
wherein in the first mode of operation a transform is applied to a first set of sampled plurality of spectral elements spaced at a first frequency interval to derive a first set of spatial domain data; and
wherein in the second mode of operation a transform is applied to a second set of sampled plurality of spectral elements spaced at a second frequency interval different from the first frequency interval to derive a second set of spatial domain data.

* * * * *

UNITED STATES PATENT AND TRADEMARK OFFICE
CERTIFICATE OF CORRECTION

PATENT NO. : 8,529,062 B2
APPLICATION NO. : 13/686214
DATED : September 10, 2013
INVENTOR(S) : Buckland et al.

It is certified that error appears in the above-identified patent and that said Letters Patent is hereby corrected as shown below:

On Title Page:
Item (63) Related U.S. Application Data:

Please correct "Continuation of application No. 12/867,891,"
to read -- Continuation of application No. 12/887,891, --

In the Specification:
Column 1, Line 30: Please correct "(-2.0-10.0 µm)"
to read -- (~2.0-10.0 µm) --

Column 9, Line 55, Item (4): Please correct the equation below:

" $z_{6\,dB} = \dfrac{2\ln(2)}{\delta_r k} = \dfrac{2\ln(2)}{\pi} \dfrac{\lambda_0^2}{\delta_r \lambda}$ "

to read

-- $z_{6dB} = \dfrac{2\ln(2)}{\delta_r k} = \dfrac{\ln(2)}{\pi} \dfrac{\lambda_0^2}{\delta_r \lambda}$ --

Column 11, Line 4: Please correct "for 8 in becomes:"
to read -- for δ in becomes: --

Signed and Sealed this
Twenty-fifth Day of February, 2014

Michelle K. Lee
*Deputy Director of the United States Patent and Trademark Office*